(12) United States Patent
Park et al.

(10) Patent No.: US 11,653,510 B2
(45) Date of Patent: May 16, 2023

(54) ADHESIVE TRANSPARENT ELECTRODE AND METHOD OF FABRICATING THE SAME

(71) Applicant: INDUSTRY-ACADEMIC COOPERATION FOUNDATION, YONSEI UNIVERSITY, Seoul (KR)

(72) Inventors: Jin Woo Park, Seoul (KR); Jin Hoon Kim, Seoul (KR)

(73) Assignee: INDUSTRY-ACADEMIC COOPERATION FOUNDATION, YONSEI UNIVERSITY, Seoul (KR)

(*) Notice: Subject to any disclaimer, the term of this patent is extended or adjusted under 35 U.S.C. 154(b) by 1182 days.

(21) Appl. No.: 16/169,174

(22) Filed: Oct. 24, 2018

(65) Prior Publication Data
US 2019/0214593 A1 Jul. 11, 2019

(30) Foreign Application Priority Data

Jan. 5, 2018 (KR) .................. 10-2018-0001504
Jun. 7, 2018 (KR) .................. 10-2018-0065578

(51) Int. Cl.
| | | |
|---|---|---|
| *A61B 5/00* | (2006.01) | |
| *H01L 29/00* | (2006.01) | |
| *H01L 29/43* | (2006.01) | |
| *H01L 21/04* | (2006.01) | |
| *H01L 33/00* | (2010.01) | |
| *B82Y 30/00* | (2011.01) | |
| *A61N 1/04* | (2006.01) | |
| *B82Y 10/00* | (2011.01) | |

(Continued)

(52) U.S. Cl.
CPC ............ *H10K 30/82* (2023.02); *A61B 5/259* (2021.01); *A61N 1/042* (2013.01); *B82Y 10/00* (2013.01); *B82Y 15/00* (2013.01); *B82Y 30/00* (2013.01); *H01L 21/0425* (2013.01); *H01L 29/43* (2013.01); *H01L 33/002* (2013.01); *H10K 50/81* (2023.02); *H10K 50/828* (2023.02); *H10K 85/10* (2023.02); *A61B 2562/125* (2013.01); *A61B 2562/164* (2013.01); *H01L 33/0004* (2013.01); *H01L 33/18* (2013.01)

(58) Field of Classification Search
CPC ............ A61B 5/24; A61B 2560/0412; A61B 2562/0217; A61B 2562/0285; A61B 2562/08; A61B 2562/125; A61B 5/25; A61N 1/0529; A61N 1/0531; A61N 1/0534
USPC ............... 600/372, 382–388, 393; 252/500
See application file for complete search history.

(56) References Cited

PUBLICATIONS

Razak et al. "A soft and conductive PDMS-PEG block copolymer as a compliant electrode for dielectric elastomers" 2015. (Year: 2015).*

(Continued)

*Primary Examiner* — Joseph A Stoklosa
*Assistant Examiner* — Brian M Antiskay
(74) *Attorney, Agent, or Firm* — Sughrue Mion, PLLC

(57) ABSTRACT

Disclosed are an adhesive transparent electrode and a method of fabricating the same. More particularly, an adhesive transparent electrode according to an embodiment of the present disclosure includes a substrate and an adhesive silicone-based polymer matrix, in which a metal nanowire network is embedded, deposited on the substrate, wherein the adhesive silicone-based polymer matrix includes a silicone-based polymer including a silicone-based polymer base and a silicone-based polymer crosslinker; and a nonionic surfactant.

13 Claims, 22 Drawing Sheets

(51) Int. Cl.
    *A61B 5/259*     (2021.01)
    *B82Y 15/00*     (2011.01)
    *H01L 33/18*     (2010.01)

(56) References Cited

PUBLICATIONS

Oytun et al. "Fabrication of solution-processable, highly transparent and conductive electrodes via layer-by-layer assembly of functional silver nanowires". Thin Solid Films 636 (May 2017). (Year: 2017).*
Communication dated Jun. 18, 2019, issued by the Korean Intellectual Property Office in corresponding Korean Application No. 10-2018-0065578.
JinHoon Kim, et al., "Silver nanowire network embedded in polydimethylsiloxane as stretchable, transparent, and conductive substrates", Journal of Applied Polymer Science, 2016, pp. 1-7 (7 pages total).
Hojjat Madadi, et al., "Study the Effects of Different Surfactants on Hydrophilicity of Polydimethylsiloxane (PDMS)", Proceedings of the ASME 2012 11th Biennial Conference On Engineering Systems Design And Analysis ESDA2012, Nantes, France, Jul. 2-4, 2012 (5 pages total).
Mei Ying Teo, et al., "Highly Stretchable and Highly Conductive PEDOT:PSS/Ionic Liquid Composite Transparent Electrodes for Solution-Processed Stretchable Electronics", ACS Applied Materials & Interfaces, 2017, vol. 9, pp. 819-826 (9 pages total).

\* cited by examiner

ADHESIVE TRANSPARENT ELECTRODE AND METHOD OF FABRICATING THE SAME

CROSS-REFERENCE TO RELATED APPLICATION

This application claims the priority benefit of Korean Patent Application No. 10-2018-0001504, filed on Jan. 5, 2018, and Korean Patent Application No. 10-2018-0065578, filed on Jun. 7, 2018, in the Korean Intellectual Property Office, the disclosure of each of which is incorporated herein by reference.

BACKGROUND OF THE DISCLOSURE

Field of the Disclosure

The present disclosure relates to an adhesive transparent electrode and a method of fabricating the same, and more particularly, to an adhesive transparent electrode including a metal nanowire network embedded in an adhesive silicone-based polymer matrix that includes a non-ionic surfactant, thus having improved conformability and adhesiveness, and a method of fabricating the same.

Description of the Related Art

In recent years, interest in and research into wearable electronic devices have been increasing due to the development of Internet of Things (IoT), interest in well-being, etc.

In particular, since a biosensor, which detects body movement or detects a biological signal by attaching to the body, should be firmly attached to the body, it is very important to develop an electrode material having adhesiveness. In addition, if an additional process of forming an electrode on a substrate, which is required to manufacture a biosensor using an electric signal, can be omitted, process costs would be greatly reduced.

Meanwhile, there have been reported techniques for mixing polydimethylsiloxane with additives to control the properties of polydimethylsiloxane so as to have adhesiveness and high ductility. There among, a method of using a silicone-based additive similar to polydimethylsiloxane has been most reported. However, when a silicone-based additive is used, an excessive amount of additive is required and the viscosity of a solution is increased due to the additive, which causes difficulties in a solution process.

In addition, research into controlling the properties of polydimethylsiloxane so as to have adhesiveness and high ductility using ethoxylated polyethyleneimine (PEIE), which is an amine-based polymer, was recently reported. However, upon use of ethoxylated PEIE, a residual remains on a surface when detached after attachment and very high hygroscopicity is exhibited, which causes decrease in light transmittance.

Further, since all the aforementioned methods of changing the properties of polydimethylsiloxane are only capable of changing the properties of a polydimethylsiloxane material, an additional electrode formation process, such as a coating or deposition process, should be separately performed to form an electrode for fabricating an electronic device.

Therefore, there is a need for a new technology for controlling the properties of polydimethylsiloxane, which does not exhibit a great transmittance difference compared to existing polydimethylsiloxane, even with a small amount of additive and enabling easy processing due sufficiently low viscosity of liquid before hardening.

SUMMARY OF THE DISCLOSURE

Therefore, the present invention has been made in view of the above problems, and it is one object of the present invention to provide an adhesive transparent electrode allowing easy control of the properties of a silicone-based polymer with a very small amount of non-ionic surfactant due to use of a non-ionic surfactant, and a method of fabricating the adhesive transparent electrode.

It is another object of the present invention to provide an adhesive transparent electrode having high adhesiveness and thus being capable of being attached to the skin without an additional adhesive, and having adhesiveness maintained even after repeated detachment and attachment, and a method of fabricating the adhesive transparent electrode.

It is another object of the present invention to provide an adhesive transparent electrode fabricated only through heat-hardening of a silicone-based polymer, unlike a conventional method of forming an electrode on a hardened polymer substrate in another coating process, and a method of fabricating the adhesive transparent electrode.

It is yet another object of the present invention to provide an adhesive transparent electrode, electrical conductivity of which is maintained even under high strain due to the electrical characteristics of a metal nanowire network, and a method of fabricating the adhesive transparent electrode.

In accordance with an aspect of the present invention, the above and other objects can be accomplished by the provision of an adhesiveness transparent electrode, including an adhesive silicone-based polymer matrix in which a metal nanowire network is embedded, wherein the adhesive silicone-based polymer matrix includes a silicone-based polymer including a silicone-based polymer base and a silicone-based polymer crosslinker; and a non-ionic surfactant.

The adhesive transparent electrode may be fabricated by coating a dispersing solution including the silicone-based polymer base, the silicone-based polymer crosslinker, and the non-ionic surfactant on a substrate on which the metal nanowire network is formed, heat-hardening the coated dispersing solution to form the adhesive silicone-based polymer matrix in which the metal nanowire network is embedded, and separating the adhesive silicone-based polymer matrix from the substrate.

Crosslinking reaction of the silicone-based polymer may be hindered and mechanical characteristics of the adhesive silicone-based polymer matrix may be improved, due to interaction between a platinum (Pt) catalyst, present in the silicone-based polymer crosslinker, and polar functional groups, present in the non-ionic surfactant.

The metal nanowire network may be embedded in the adhesive silicone-based polymer matrix due to interaction between polar functional groups, present in the non-ionic surfactant, and polar functional groups, present in the metal nanowire network.

The non-ionic surfactant may be 4-(1,1,3,3-tetramethylbutyl)phenyl-polyethylene glycol.

The silicone-based polymer may be polydimethylsiloxane (PDMS).

A weight ratio of the polydimethylsiloxane base to the polydimethylsiloxane crosslinker to the non-ionic surfactant may be 10:1:0.01 to 10:1:0.08.

In accordance with another aspect of the present invention, there is provided a method of fabricating an adhesive transparent electrode, the method including forming a metal nanowire network on a substrate; coating a dispersing solution including a silicone-based polymer base, a silicone-based polymer crosslinker, and a non-ionic surfactant on the substrate on which the metal nanowire network is formed; and heat-hardening the dispersing solution coated on the substrate, on which the metal nanowire network is formed, to form an adhesive silicone-based polymer matrix in which the metal nanowire network is embedded.

The method may further include separating the adhesive silicone-based polymer matrix, in which the metal nanowire network is embedded, from the substrate.

The forming may include coating a metal nanowire solution on the substrate; and annealing the substrate coated with the metal nanowire solution.

The silicone-based polymer may be polydimethylsiloxane, and the metal nanowire network may be a silver (Ag) nanowire network.

The annealing may be performed at 100° C. to 180° C. for 5 minutes to 20 minutes. The heat hardening may be performed at 40° C. to 80° C. for 8 hours to 12 hours. The adhesive transparent electrode according to an embodiment of the present disclosure may be applied to an optoelectronic device, an electrocardiogram (ECG) sensor, an electromyogram (EMG) sensor and a transparent film heater.

BRIEF DESCRIPTION OF THE DRAWINGS

The above and other objects, features and advantages of the present disclosure will become more apparent to those of ordinary skill in the art by describing exemplary embodiments thereof in detail with reference to the accompanying drawings, in which.

DETAILED DESCRIPTION OF THE DISCLOSURE

Figure 1:
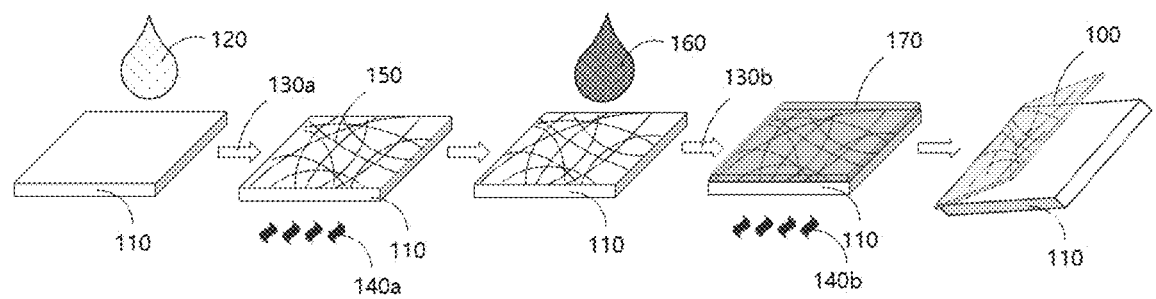
FIG. 1 is a view illustrating a method of fabricating an adhesive transparent electrode according to an embodiment of the present disclosure.

The present disclosure will now be described more fully with reference to the accompanying drawings and contents disclosed in the drawings. However, the present disclosure should not be construed as limited to the exemplary embodiments described herein.

The terms used herein are for the purpose of describing particular embodiments only and is not intended to be limiting of the inventive concept.

It will be understood that the terms, such as "comprises," "have," and "provided," used in this specification, specify the presence of stated features, integers, steps, operations, elements, components, or combinations thereof, but do not preclude the presence or addition of one or more other features, integers, steps, operations, elements, components, or combinations thereof.

In addition, it should not be understood that arbitrary aspects or designs disclosed in "embodiments", "examples", "aspects", etc. used in the specification are more satisfactory or advantageous than other aspects or designs.

In addition, the expression "or" means "inclusive or" rather than "exclusive or". That is, unless otherwise mentioned or clearly inferred from context, the expression "x uses a or b" means any one of natural inclusive permutations.

Further, as used in the description of the disclosure and the appended claims, the singular forms "a", "an" and "the" are intended to include the plural forms as well, unless context clearly indicates otherwise.

In addition, when an element such as a layer, a film, a region, and a constituent is referred to as being "on" another element, the element can be directly on another element or an intervening element can be present.

In addition, it will be understood that, although the terms first, second, third etc. may be used herein to describe various elements, these elements should not be limited by these terms. These terms are only used to distinguish one element from another element. For example, a first element may be termed a second element and a second element may be termed a first element without departing from the teachings of the present disclosure.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Hereinafter, the present disclosure will be described in detail by explaining particular embodiments of the disclosure with reference to the attached drawings. However, it should be understood that the spirit and scope of the present disclosure are not limited to the embodiments and can be modified by addition, modification, or deletion of elements constituting the embodiments and such additions, modifications, and deletions are also within the spirit and scope of the present disclosure.

The present disclosure relates to an adhesive transparent electrode and a method of fabricating the same, and more particularly, to a transparent electrode fabricated by adding an additive (non-ionic surfactant) to a silicone-based polymer and thus having excellent ductility and adhesiveness, and a method of fabricating the same.

FIG. 1 is a view illustrating a method of fabricating an adhesive transparent electrode according to an embodiment of the present disclosure.

Referring to FIG. 1, an adhesive transparent electrode according to an embodiment of the present disclosure may be fabricated using a substrate, a silicone-based polymer, a non-ionic surfactant, and a metal nanowire network.

A metal nanowire solution 120 may be coated on a substrate 110 (130*a*), and then a metal nanowire network 150 may be formed on the substrate 110 by annealing (140*a*).

The substrate 110 may include a transparent material capable of transmitting light, e.g., a silicone substrate, a glass substrate, or a polymer substrate, but the present disclosure is not limited thereto.

The silicone substrate may include a single silicone substrate or p-Si substrate, and the glass substrate may be formed of any one of alkali silicate glass, non-alkali glass, and quartz glass or a combination thereof. However, the silicone substrate and the glass substrate may be formed of various materials without being limited to the aforementioned materials.

The polymer substrate may be formed of any one of polyethylene terephthalate (PET), polyethylene naphthalate (PEN), polyimide (PI), and polyurethane, or a combination thereof. However, the polymer substrate may be formed of various materials without being limited to the aforementioned materials. The polymer substrate is not specifically limited so long as it has sufficient transparency and flexibility to be used in a transparent flexible display.

The metal nanowire solution 120 may be formed of various materials. Particularly, the metal nanowire solution 120 may be a silver nanowire solution.

The metal nanowire solution 120 may be spin-coated on the substrate, but the present disclosure is not specifically limited thereto. The metal nanowire solution 120 may be coated on the substrate by other known methods varying a rotation speed and time.

In particular, the metal nanowire solution 120 may be coated on the substrate in a spin coating manner, a spray coating manner, an inkjet coating manner, a slit coating manner, a deep coating manner, or the like, without being specifically limited thereto. The metal nanowire solution 120 is spin-coated on the substrate 110 at 400 rpm to 1000 rpm for 30 seconds to 60 seconds (130*a*), and then an annealing process (140*a*) is performed to evaporate and dry a solvent.

For example, when the metal nanowire solution is a silver nanowire solution, a nanowire network 150 may be formed by annealing the silver nanowire solution at 100° C. to 180° C. for 5 minutes to 20 minutes.

Subsequently, a dispersing solution 160 including a silicone-based polymer base, a silicone-based polymer crosslinker, and a non-ionic surfactant is coated on the substrate 110 coated with the metal nanowire network 150.

The silicone-based polymer may be made of, without being limited to, any one of cyclomethicone, dimethicone, phenyl trimethicone, amodimethicone, polydimethylsiloxane, phenyl siloxane, alkylmethyl siloxane, and dimethicone copolyol, or a combination thereof, and may be made of various materials. Particularly, the silicone-based polymer may be polydimethylsiloxane.

For example, when the silicone-based polymer is polydimethylsiloxane, the dispersing solution 160 may be prepared by mixing a polydimethylsiloxane base, a polydimethylsiloxane crosslinker, and a non-ionic surfactant in a weight ratio of 10:1:0.01 to 10:1:0.08, particularly in a weight ratio of 10:1:0.03 to 10:1:0.05.

The polydimethylsiloxane base may be a commercial product and may be represented by Formula 1 below:

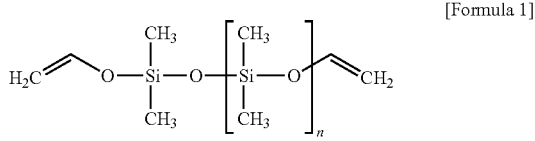

[Formula 1]

The polydimethylsiloxane crosslinker may be a material represented by Formula 2 below:

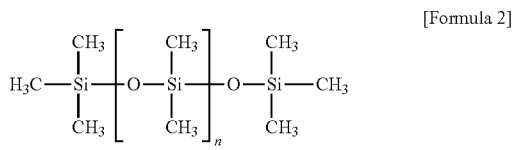

[Formula 2]

The non-ionic surfactant may be formed of any one of 4-(1,1,3,3-tetramethylbutyl)phenyl-polyethylene glycol, fatty alcohol-polyoxyethylene ether, polyoxyethylene sorbitan fatty acid esters, polyoxyethylene fatty acid ester, polyoxyethylene alkylether, sorbitan esters, glyceryl esters, glyceryl monostearate, polyethylene glycol, polypropylene glycol, polypropylene glycol esters, cetyl alcohol, cetostearyl alcohol, stearyl alcohol, or a combination thereof. However, the non-ionic surfactant may be formed of various materials without being limited to the aforementioned materials.

Particularly, the non-ionic surfactant may be 4-(1,1,3,3-tetramethylbutyl)phenyl-polyethylene glycol represented by Formula 3 below:

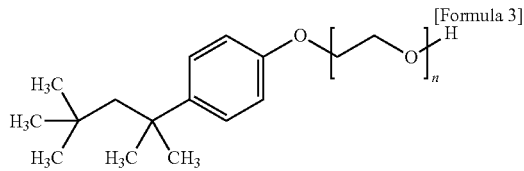

[Formula 3]

Bubbles in the dispersing solution 160 may be removed by degassing. The properties of the dispersing solution 160 may be controlled by a non-ionic surfactant included therein.

The dispersing solution 160 may be spin-coated the substrate 110 coated with the metal nanowire network 150, but the present disclosure is not limited to this coating manner. The dispersing solution 160 may be coated in other known manners varying a rotation speed and time.

In particular, the dispersing solution 160 may be coated in a spin coating manner, a spray coating manner, an inkjet coating manner, a slit coating manner, a deep coating manner, or the like, without being specifically limited thereto.

The dispersing solution 160 is spin-coated on the substrate 110 coated with the metal nanowire network 150 at 3 rpm to 400 rpm for 15 seconds to 30 seconds (130b), and then a heat hardening process (140b) is performed.

For example, when the metal nanowire network 150 is a nanowire network, the heat hardening may be performed at 40° C. to 80° C. for 8 hours to 12 hours, thereby forming the adhesive polydimethylsiloxane matrix 170 in which a nanowire network has been embedded.

Subsequently, the heat-hardened adhesive silicone-based polymer matrix 170 is detached from the substrate 110, thereby forming an adhesive transparent electrode 100 in which the metal nanowire network has been embedded.

In the case of the adhesive transparent electrode based on the adhesive silicone-based polymer matrix according to an embodiment of the present disclosure, a silicone-based polymer matrix including a metal nanowire network on a surface thereof may be fabricated by heat-hardening a silicone-based polymer and then separating the hardened silicone-based polymer from a substrate, unlike a conventional method of forming an electrode on a heat-hardened polymer substrate in a coating process, etc. Accordingly, the adhesive transparent electrode based on the adhesive silicone-based polymer matrix according to an embodiment of the present disclosure may be simply formed without an additional process of forming an electrically conductive material.

Hereinafter, the characteristics of an adhesive silicone-based polymer matrix according to an embodiment of the present disclosure and an adhesive transparent electrode based on the adhesive silicone-based polymer matrix are described.

EXAMPLE (Preparation of Dispersing Solution)

Dispersing solutions were prepared by mixing polydimethylsiloxane base, polydimethylsiloxane crosslinker, and 4-(1,1,3,3-tetramethylbutyl)phenyl-polyethylene glycol (hereinafter referred to as "Triton X-100") in various weight ratios of 10:1:0 to 10:1:0.08.

A weight ratio of the polydimethylsiloxane base to the polydimethylsiloxane crosslinker was fixed to 10:1.

(Fabrication of Adhesive Transparent Electrode)

A slide glass (Paul Marienfeld GmbH & Co. KG, Germany), which was used as a substrate was sequentially washed with acetone, 2-propanol, and deionized water for 10 minutes in an ultrasonic bath, respectively. The washed slide glass was dried using an air gun.

0.65% by weight of a silver nanowire solution (manufactured by Novarials) having an average length of 30 μm and a diameter of 30 nm was spin-coated on the substrate at 500 rpm for 60 seconds, followed by annealing at 100° C. for 5 minutes so as to evaporate a solvent therefrom.

A dispersing solution was spin-coated on the substrate, coated with the silver nanowire solution, at 300 rpm for 15 seconds, followed by heat hardening at 40° C. to 80° C. for 11 hours.

Subsequently, the hardened adhesive polydimethylsiloxane matrix was immersed in a bath containing deionized water for 5 minutes at room temperature, and then the adhesive transparent electrode, in which the nanowire network was embedded, was removed from the substrate in the state in which it was immersed in the deionized water.

COMPARATIVE EXAMPLE (Preparation of Dispersing Solution)

A dispersing solution was prepared by mixing a polydimethylsiloxane base and polydimethylsiloxane crosslinker in a weight ratio of 10:1.

(Fabrication of Transparent Electrode)

A slide glass (Paul Marienfeld GmbH & Co. KG, Germany), which was used as a substrate was sequentially washed with acetone, 2-propanol, and deionized water for 10 minutes in an ultrasonic bath, respectively. The washed slide glass was dried using an air gun.

0.65% by weight of a silver nanowire solution (manufactured by Novarials) having an average length of 30 μm and a diameter of 30 nm was spin-coated on the substrate at 500 rpm for 60 seconds, followed by annealing at 100° C. for 5 minutes so as to evaporate a solvent therefrom.

A dispersing solution was spin-coated on the substrate, coated with the silver nanowire solution, at 300 rpm for 15 seconds, followed by heat hardening at 40° C. to 80° C. for 11 hours.

Subsequently, the hardened polydimethylsiloxane matrix was immersed in a bath containing deionized water for 5 minutes at room temperature, and then the polydimethylsiloxane matrix, in which the nanowire network was embedded, was removed from the substrate in the state in which it was immersed in the deionized water.

To examine the characteristics of the adhesive polydimethylsiloxane matrix according to an embodiment of the present disclosure, a Triton X-100 content (% by weight) in the adhesive polydimethylsiloxane matrix and hardening temperature ($T_a$) thereof were varied. Used samples are summarized in Table 1 below.

TABLE 1

| Sample name | Triton X-100 content (% by weight) in adhesive polydimethylsiloxane matrix | Heat hardening temperature ($T_c$) (° C.) |
|---|---|---|
| PDMS_40 | 0 | 40 |
| PDMS_70 | | 70 |
| a3-PDMS_40 | 0.3 | 40 |
| a3-PDMS_50 | | 50 |
| a3-PDMS_70 | | 70 |
| a4-PDMS_40 | 0.4 | 40 |
| a4-PDMS_50 | | 50 |
| a4-PDMS_70 | | 70 |
| a5-PDMS_40 | 0.5 | 40 |
| a8-PDMS_40 | 0.8 | 40 |

Figure 2A:
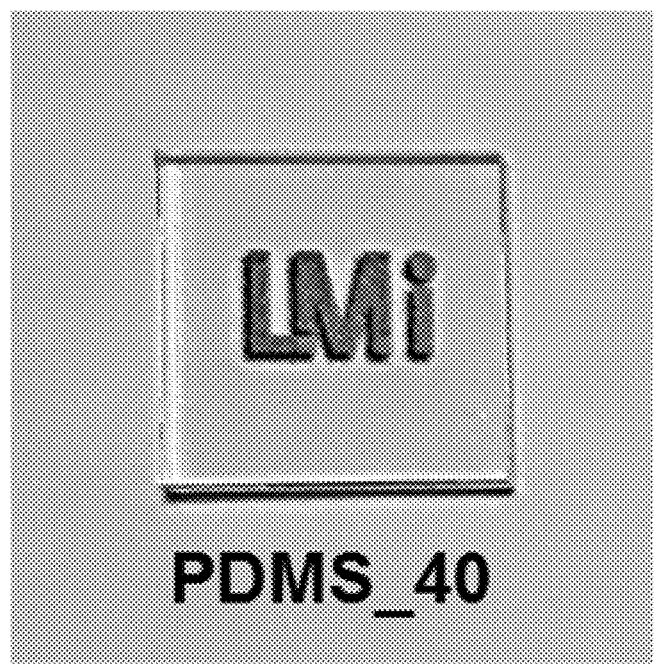
FIGS. 2A to 2E illustrate adhesive polydimethylsiloxane matrix images dependent upon a Triton X-100 content in an adhesive polydimethylsiloxane matrix according to an embodiment of the present disclosure.
Figure 2B:
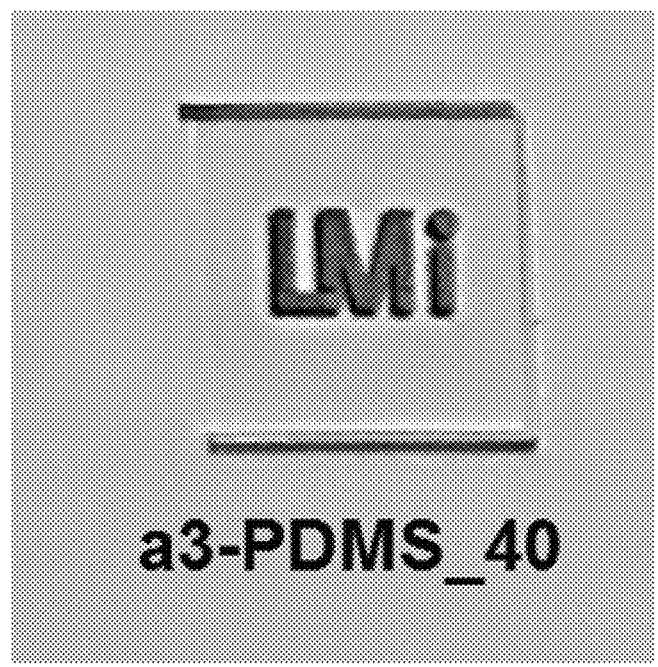
Figure 2C:
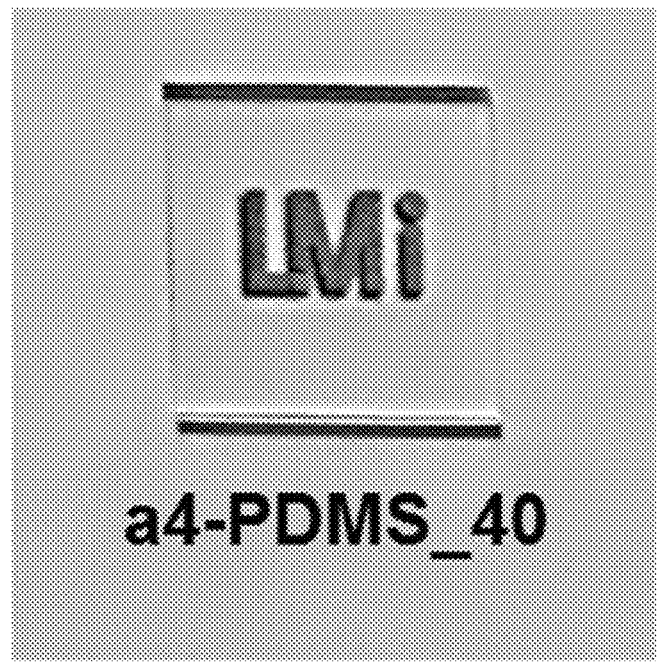
Figure 2D:
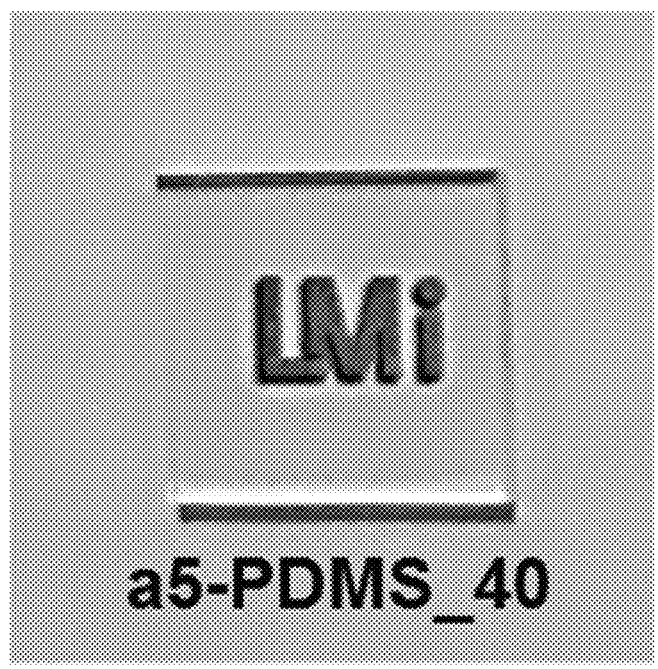
Figure 2E:
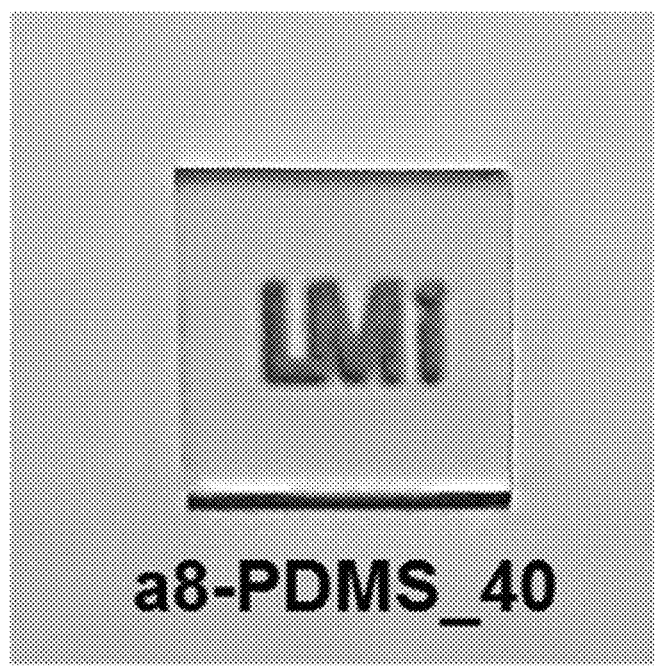
Figure 2F:
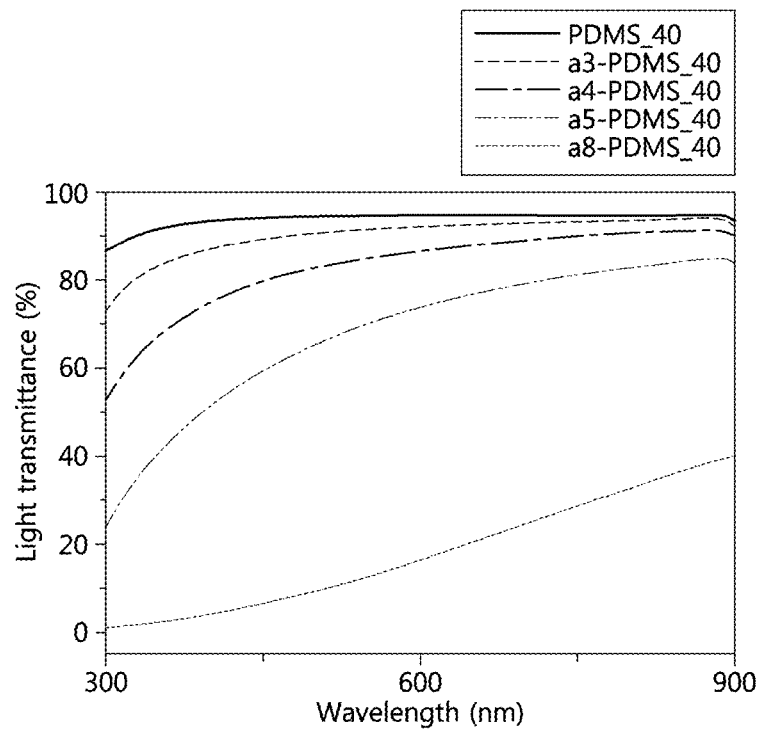
FIG. 2F is a graph illustrating light transmittances dependent upon a Triton X-100 content in an adhesive polydimethylsiloxane matrix.

FIGS. 2A to 2E illustrate adhesive polydimethylsiloxane matrix images dependent upon a Triton X-100 content in an adhesive polydimethylsiloxane matrix according to an embodiment of the present disclosure, and FIG. 2F is a graph illustrating light transmittances dependent upon a Triton X-100 content in an adhesive polydimethylsiloxane matrix.

Referring to FIGS. 2A to 2E, a Triton X-100 content in the adhesive polydimethylsiloxane matrix was adjusted to 0%, 0.3%, 0.4%, 0.5%, and 0.8% at a heat hardening temperature of 40° C. As a result, it can be confirmed that light scattering of the adhesive polydimethylsiloxane matrix is worsened with increasing Triton X-100 content.

Referring to FIG. 2F, it can be confirmed that light transmittance (T) of the adhesive polydimethylsiloxane matrix is decreased with increasing Triton X-100 content, and influence of heat hardening temperature ($T_a$) on the light transmittance of the adhesive polydimethylsiloxane matrix is negligible.

A polydimethylsiloxane matrix (PDMS_40) excluding Triton X-100 exhibits a highest light transmittance value of 94.3% at a wavelength of 550 nm. It can be confirmed that light transmittance values of an adhesive polydimethylsiloxane matrix with 0.3% by weight of Triton X-100 (hereinafter referred to as "a3-PDMS_40") and an adhesive polydimethylsiloxane matrix mixed with 0.4% by weight of Triton X-100 (hereinafter referred to as "a4-PDMS_40) are respectively 91.4% and 84.7% which are lower than that of PDMS_40.

To fabricate a transparent electrode based on the adhesive polydimethylsiloxane matrix, the adhesive polydimethylsiloxane matrix should have a light transmittance of 80% or more. Therefore, a3-PDMS_40 and a4-PDMS_40 were selected for subsequent analysis.

Light transmittance is decreased with increasing Triton X-100 content because light scatters due to a micelle structure formed in a polydimethylsiloxane matrix mixed with Triton X-100. Since the polydimethylsiloxane matrix is very hydrophobic, alkyls in a Triton X-100 chain form a shell, whereas corresponding polyethylene glycol (PEG) forms a core of the micelle structure.

In addition, it is known that the size of micelle increases with increasing surfactant concentration, whereby light scattering intensity also increases.

Figure 3A:
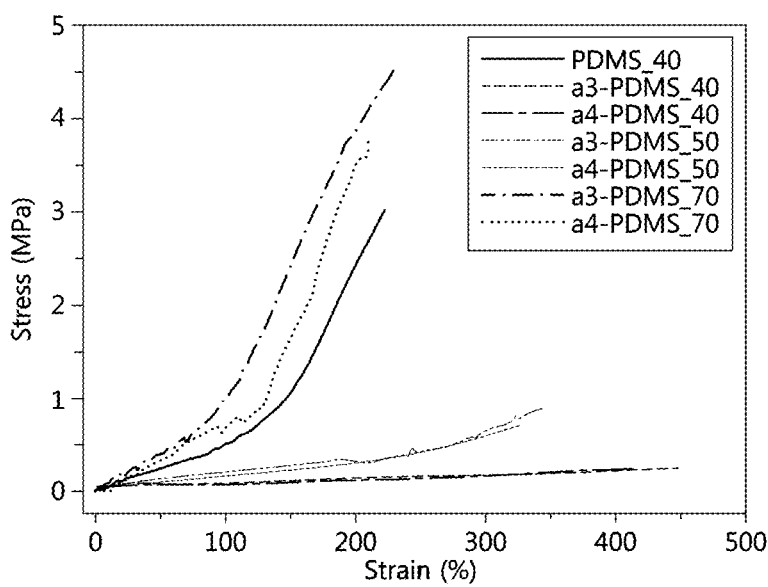
FIG. 3A illustrates stress-strain curves of adhesive polydimethylsiloxane matrixes according to an embodiment of the present disclosure.
Figure 3B:
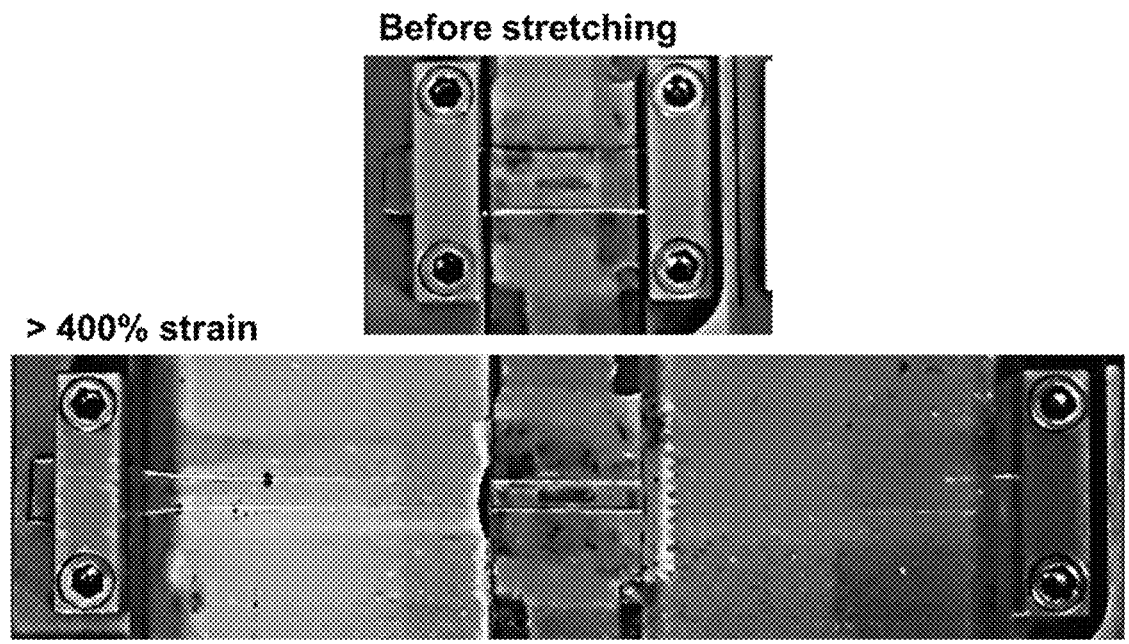
FIG. 3B illustrates an image of a4-PDMS_40 under a uniaxial stretching test.

FIG. 3A illustrates stress-strain curves of adhesive polydimethylsiloxane matrixes according to an embodiment of the present disclosure, and FIG. 3B illustrates an image of a4-PDMS_40 under a uniaxial stretching test.

Young's moduli and failure strains of a polydimethylsiloxane matrix, and adhesive polydimethylsiloxane matrixes, which respectively included 0.3% by weight of Triton X-100 and 0.4% by weight of Triton X-100, fabricated while varying a heat hardening temperature at 40° C., 50° C. and 70° C. were only measured.

In addition, a stretching speed was fixed to 1 mm·sec$^{-1}$, temperature was maintained at 20° C., and Young's modulus was calculated from 0% to 100% strain.

A polydimethylsiloxane matrix sample and adhesive polydimethylsiloxane matrix samples used to measure Young's modulus and failure strain and measurement results thereof are summarized in Table 2 below.

TABLE 2

| Sample | Young's modulus (kPa) | Failure strain (%) |
|---|---|---|
| PDMS_40 | 480 ± 30 | 230 |
| a3-PDMS_40 | 38 ± 6.3 | >400 |
| a4-PDMS_40 | 40 ± 5 | >400 |
| a3-PDMS_50 | 194 ± 7.2 | >300 |
| a4-PDMS_50 | 162 ± 20 | >300 |
| a3-PDMS_70 | 1000 ± 50 | 220 |
| a4-PDMS_70 | 810 ± 20 | 210 |

Referring to FIG. 3A and Table 2, it can be confirmed that a3-PDMS_40 and a4-PDMS_40 exhibit the lowest Young's modulus and the highest failure strain among all the samples.

Young's modulus and failure strain of PDMS_40 are respectively 500 kPa and 230%. On the other hand, a3-PDMS_40 and a4-PDMS_40 respectively exhibit Young's moduli of 38 kPa and 40 kPa, and both exhibit a failure strain of 400% or more.

The Young's moduli of a3-PDMS_40 and a4-PDMS_40 are much lower than Young's modulus of human skin of 500 kPa to 1 MPa. From these results, it can be confirmed that a3-PDMS_40 and a4-PDMS_40 are suitable for epidermal electronics.

Conformability of an electrode increases with decreasing Young's modulus of a polymer matrix. Accordingly, when the adhesive polydimethylsiloxane matrix has a lower Young's modulus than the skin, a contact area between an electrode and the skin expands, and a user feels more comfortable.

In addition, referring to FIG. 3A, it can be confirmed that Young's modulus increases with increasing heat hardening temperature of the adhesive polydimethylsiloxane matrix. Conventionally, the elastic modulus of polydimethylsiloxane was lowered by reducing the amount of a polydimethylsiloxane crosslinker, whereby the failure strain of polydimethylsiloxane was also deteriorated.

In contrast, a3-PDMS_40 and a4-PDMS_40 exhibit highly reinforced failure strain, which indicates that a3-PDMS_40 and a4-PDMS_40 are suitable candidate materials for a transparent and stretchable polymer matrix used in epidermal electronic devices.

Referring to FIG. 3B, a4-PDMS_40 is not fractured even under a strain of 400% or more.

Figure 4:
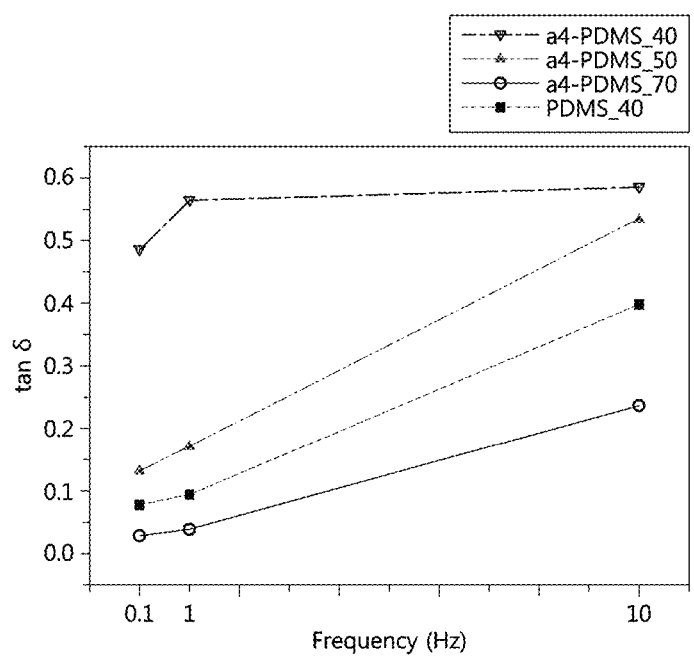
FIG. 4 illustrates viscoelasticity of an adhesive polydimethylsiloxane matrix according to an embodiment of the present disclosure.

FIG. 4 illustrates viscoelasticity of an adhesive polydimethylsiloxane matrix according to an embodiment of the present disclosure.

Viscoelasticity of a polydimethylsiloxane matrix and adhesive polydimethylsiloxane matrixes was measured by means of a dynamic mechanical analyzer. In addition, the viscoelasticity of the polydimethylsiloxane matrix and the adhesive polydimethylsiloxane matrixes was determined according to Equation (1):

$$\tan\delta = \frac{E''}{E'} = \frac{\text{Viscous loss modulus}}{\text{Elastic storage modulus}} \quad (1)$$

tan δ denotes a loss tangent, E' denotes elasticity of an elastic body, and E" denotes viscoelasticity of an elastic body. Accordingly, an elastic body exhibits higher viscoelasticity behavior as it has a higher loss tangent (tan δ).

For reference, since a3-PDMS_40 and a4-PDMS_40 exhibited similar results in a uniaxial stretching test, the polydimethylsiloxane matrix and the adhesive polydimethylsiloxane matrix including 0.4% by weight of Triton X-100 were only subjected to viscoelasticity analysis.

Referring to FIG. 4, it can be confirmed that loss tangents of PDMS_40, a4-PDMS_40, a4-PDMS 50, and a4-PDMS 70 increase with decreasing hardening temperature thereof. In addition, it can be confirmed that a4-PDMS_40 exhibits a high loss tangent of about 0.5 even at a low frequency of 0.1 Hz.

Conventionally, the loss tangent of silicone rubber was reported to be less than 0.4 or less than 0.1. Accordingly, it can be confirmed that a4-PDMS_40 exhibits very high viscoelasticity, compared to other silicone-based elastic bodies.

From the aforementioned uniaxial stretching test results and viscoelasticity measurement results, it can be confirmed that the adhesive polydimethylsiloxane matrixes fabricated by adding 0.3 or 0.4% by weight of Triton X-100 at a hardening temperature of 40° C. have higher flexibility and viscoelasticity, compared to the polydimethylsiloxane matrix excluding Triton X-100.

Figure 5A:
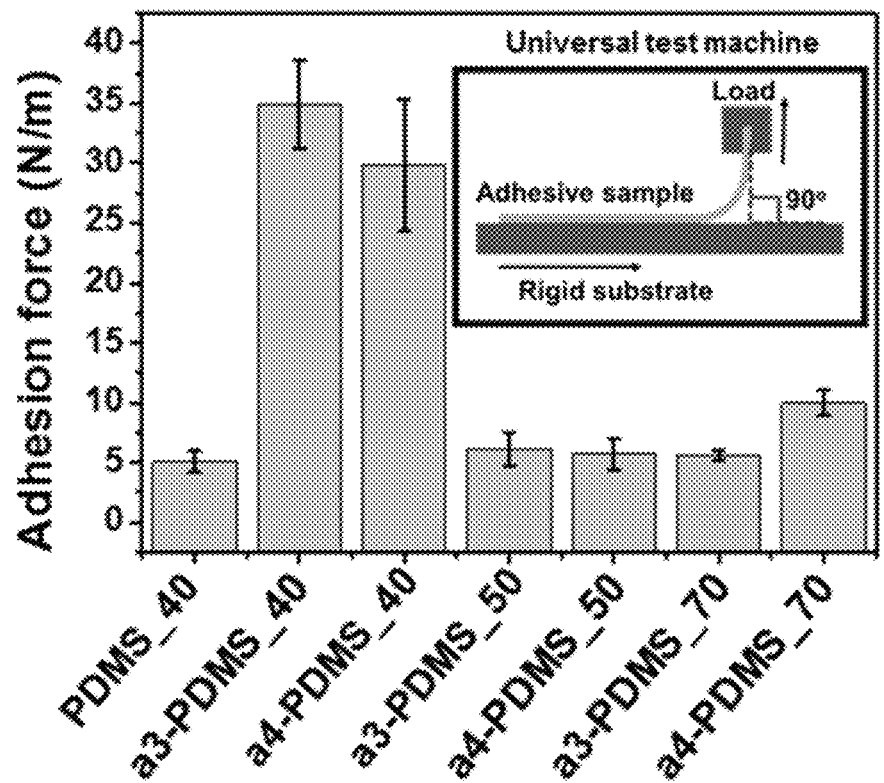
FIG. 5A illustrates adhesion force of an adhesive polydimethylsiloxane matrix according to an embodiment of the present disclosure measured by a peel test.
Figure 5B:
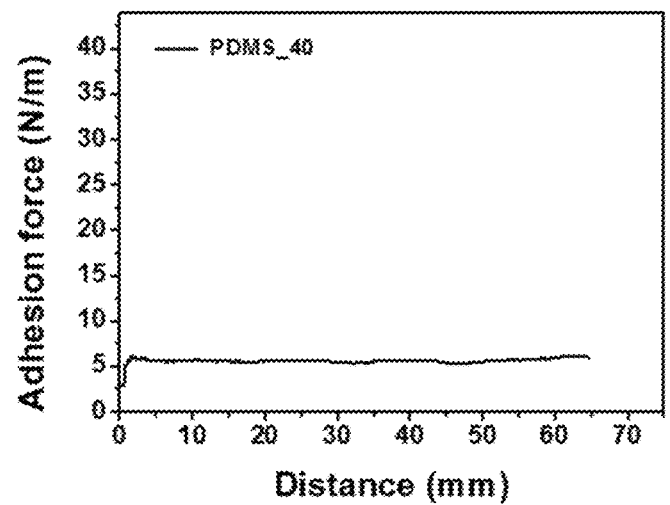
FIGS. 5B to 5H illustrate adhesion force measured by a peel test.
Figure 5C:
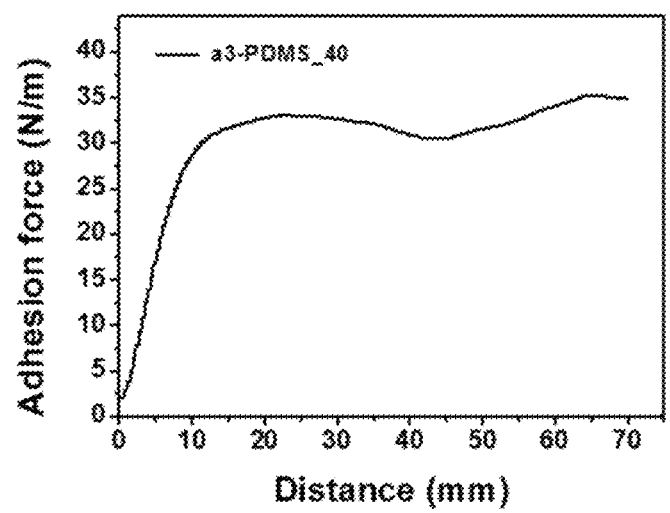
Figure 5D:
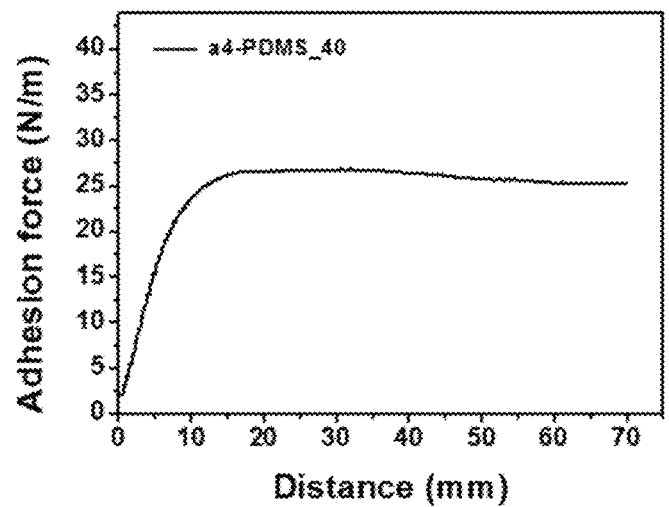
Figure 5E:
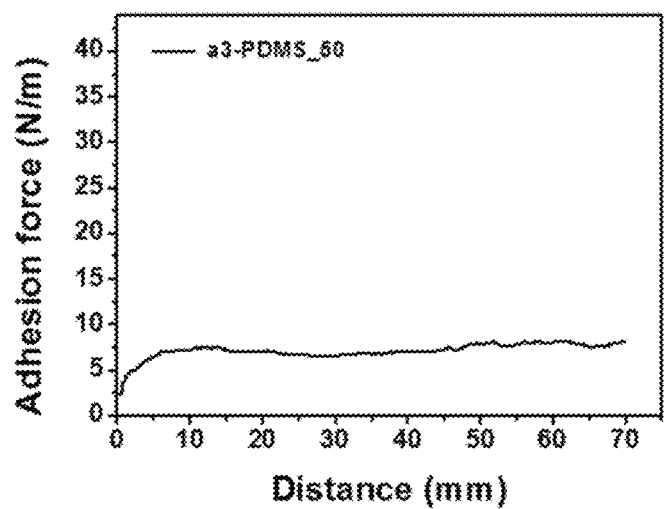
Figure 5F:
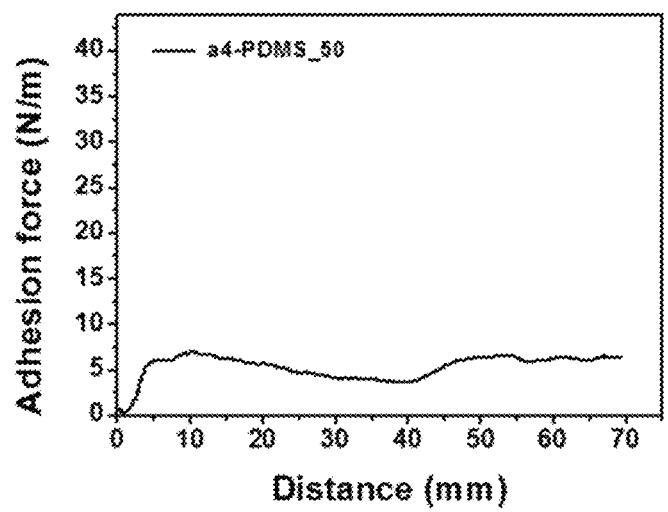
Figure 5G:
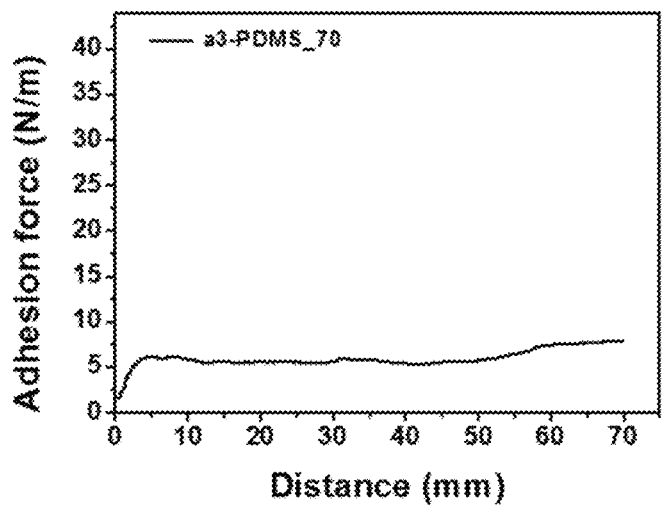
Figure 5H:
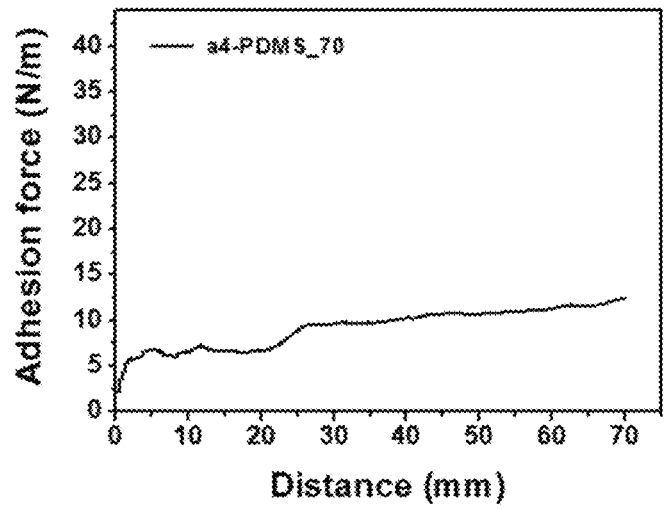
Figure 5I:
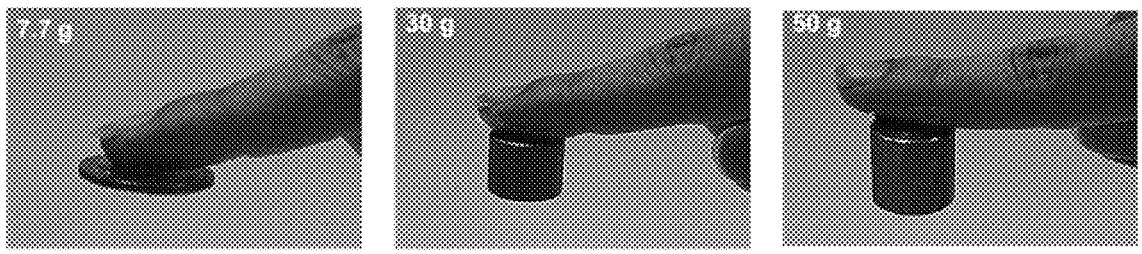
FIG. 5I illustrates images of an adhesive polydimethylsiloxane matrix supporting various weights.

FIG. 5A illustrates adhesion force of an adhesive polydimethylsiloxane matrix according to an embodiment of the present disclosure measured by a peel test, FIGS. 5B to 5H illustrate adhesion force measured by a peel test, and FIG. 5I illustrates images of an adhesive polydimethylsiloxane matrix supporting various weights.

To measure adhesion force of the polydimethylsiloxane matrix and the adhesive polydimethylsiloxane matrix, a peel test was conducted according to ASTM D3330 standard at a peel angle of 90°. A test device therefor is illustrated in an upper left image inserted in FIG. 5A.

For the adhesion force measurement, the size of a sample was 100 mm×25 mm, a peeling speed was fixed to 300 mm min$^{-1}$, and the force of a load cell was 20 N. In addition, a test environment was maintained at 25±2° C. under a relative humidity of 45±5%.

Referring to FIG. 5A, a3-PDMS_40 and a4-PDMS_40 exhibit highest adhesion force among all the samples. It can be confirmed that the adhesion force of a3-PDMS_40 is 35 Nm$^{-1}$ which is 7 times higher than that of the polydimethylsiloxane matrix.

Referring adhesion force-distance graphs of the samples measured by a peel test illustrated in FIGS. 5B to 5H, it can be confirmed that the adhesion force of a3-PDMS_40 and a4-PDMS_40 is highest.

Referring to FIG. 5I, 7.7 g of a coin, 30 g of a brass block, and 50 g of a brass block were respectively attached to the fingers using a4-PDMS_40. As results, it can be confirmed that even the brass block of 50 g may be maintained in a state of being completely attached to the finger by a4-PDMS_40.

From FIGS. 5A to 5I, it can be confirmed that heat hardening temperature affects the adhesion force of the adhesive polydimethylsiloxane matrix. It can be confirmed that the very low elastic modulus and the very high viscoelasticity of the adhesive polydimethylsiloxane matrix heat-hardened at 40° C. improve wetting and spreading of chains therein, which increases surface contact and the adhesion force of the adhesive polydimethylsiloxane matrix.

Figure 6A:
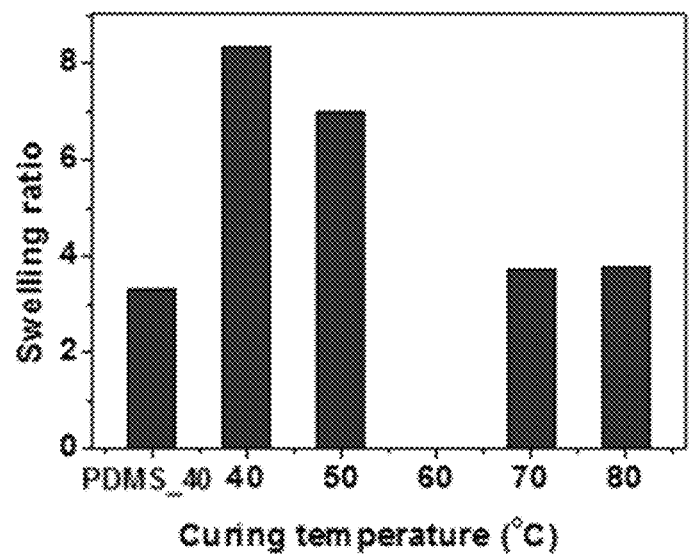
FIGS. 6A and 6B illustrate a swelling ratio of an adhesive polydimethylsiloxane matrix according to an embodiment of the present disclosure.
Figure 6B:
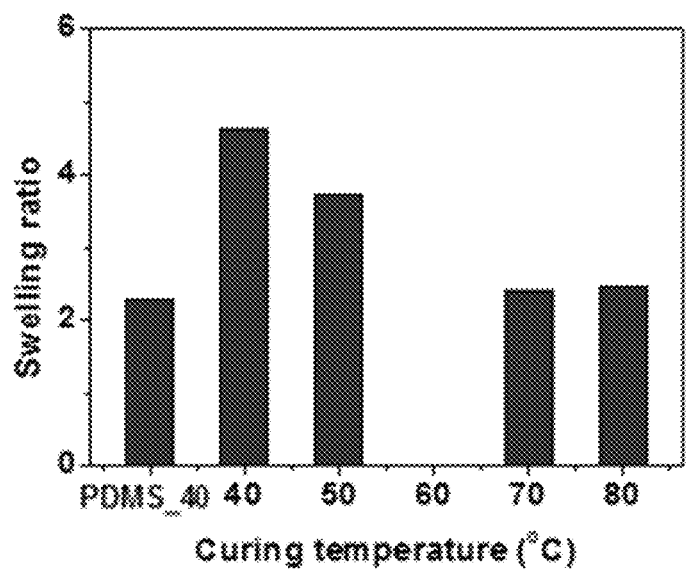
Figure 6C:
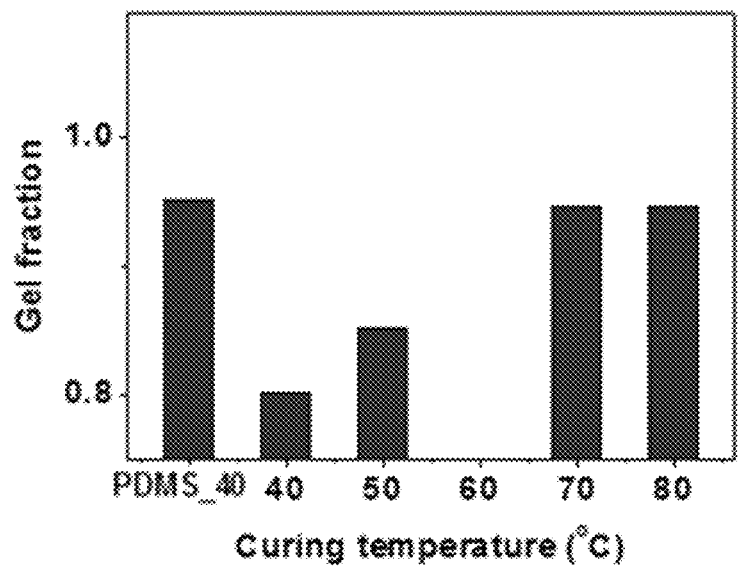
FIGS. 6C and 6D illustrate a gel fraction.
Figure 6D:
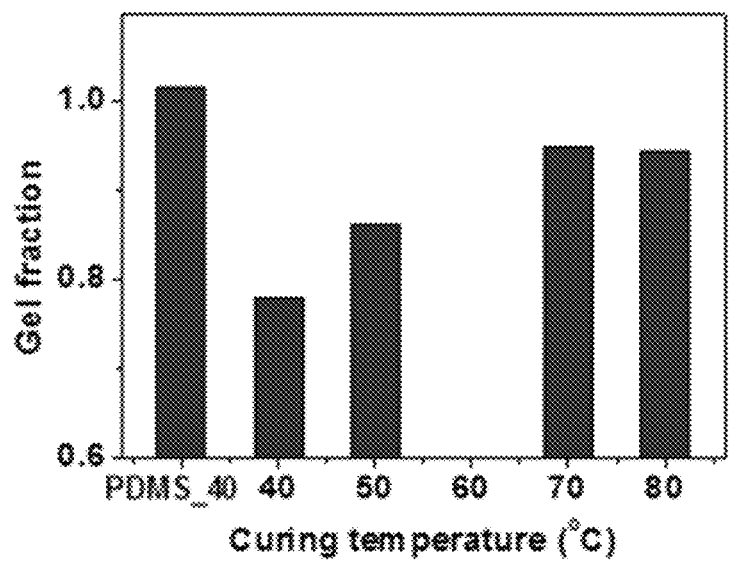

FIGS. 6A and 6B illustrate a swelling ratio of an adhesive polydimethylsiloxane matrix according to an embodiment of the present disclosure, and FIGS. 6C and 6D illustrate a gel fraction.

Optical properties of an adhesive polydimethylsiloxane matrix are greatly affected by a Triton X-100 content therein, and mechanical properties, such as Young's modulus, failure strain, viscoelasticity, and adhesion force, greatly affect a heat hardening temperature of an adhesive polydimethylsiloxane matrix.

To explain influence of a Triton X-100 content on Young's modulus, viscoelasticity and adhesion force, swelling ratios and gel fractions of the adhesive polydimethylsiloxane matrix and polydimethylsiloxane matrixes were measured. As a solvent therefore, chloroform and toluene were used.

Referring to FIGS. 6A and 6B, it can be confirmed that swelling ratios of a4-PDMS_40 in chloroform and toluene are respectively 2.5 times and 2 times higher than those of PDMS_40.

In addition, referring to FIGS. 6C and 6D, it can be confirmed that gel fractions of a4-PDMS_40 in chloroform and toluene are respectively 0.8 and 0.77, and gel fractions of PDMS_40 in chloroform and toluene are respectively 0.95 and 1.0.

In particular, swelling ratios and gel fractions of a4-PDMS and PDMS_40 in chloroform and toluene solvents are represented by functions to hardening temperature, and the swelling ratios and the gel fractions are respectively determined by Equations (2) and (3) below:

$$\text{swelling ratio} = \frac{\text{weight of swollen sample}}{\text{weight of initital sample}} \quad (2)$$

$$\text{Gel fraction} = \frac{\text{weight of deswollen sample}}{\text{weight of initial sample}} \quad (3)$$

As shown in FIGS. 6A and 6B, in chloroform and toluene, the swelling ratios of a4-PDMS_40 are respectively 2.5 times and 2 times higher than those of PDMS_40. Accordingly, the swelling ratio of the adhesive polydimethylsiloxane matrix is decreased with increasing heat hardening temperature, and becomes similar to that of the adhesive polydimethylsiloxane matrix at a heat hardening temperature of 70° C. or more.

In addition, as shown in FIGS. 6C and 6D, the gel fractions of a4-PDMS_40 in chloroform and toluene were respectively 0.8 and 0.77, and the gel fractions of PDMS_40 in chloroform and toluene were respectively 0.95 and 1.0. Similar to the swelling ratio result, the gel fraction of the adhesive polydimethylsiloxane matrix increases with increasing heat hardening temperature, and becomes similar to that of the polydimethylsiloxane matrix at a heat hardening temperature of 70° C. or more.

Crosslinking of polydimethylsiloxane occurs via hydrosilylation using a platinum (Pt) catalyst. The Pt catalyst diffuses through a polydimethylsiloxane matrix to complete a crosslinking reaction. The Pt catalyst forms a complex with other polar functional groups, such as a PEG chain of Triton X-100, because it is coordinately unsaturated.

In addition, Triton X-100 forms a core-shell structure inside a polydimethylsiloxane matrix. Therefore, when nonpolar functional groups surround platinum-interacting polar groups of Triton X-100 having a core-shell structure inside the polydimethylsiloxane matrix, the amount of an active Pt catalyst present in the polydimethylsiloxane matrix is reduced.

Accordingly, crosslinking reaction is hindered by adding a small amount of Triton X-100 to a polydimethylsiloxane mixture to cause inactivation of a Pt catalyst, which is a main mechanism for forming a heterogeneously crosslinked network in polydimethylsiloxane. Due to Triton X-100 molecules, a heterogeneously crosslinked network composed of crosslinked polydimethylsiloxane and non-crosslinked polydimethylsiloxane is formed in the adhesive polydimethylsiloxane matrix.

This composite structure modulates mechanical properties, such as Young's modulus, failure strain, viscoelasticity, and adhesion force, and thus, forms a soft and adhesive polydimethylsiloxane matrix.

Figure 7A:
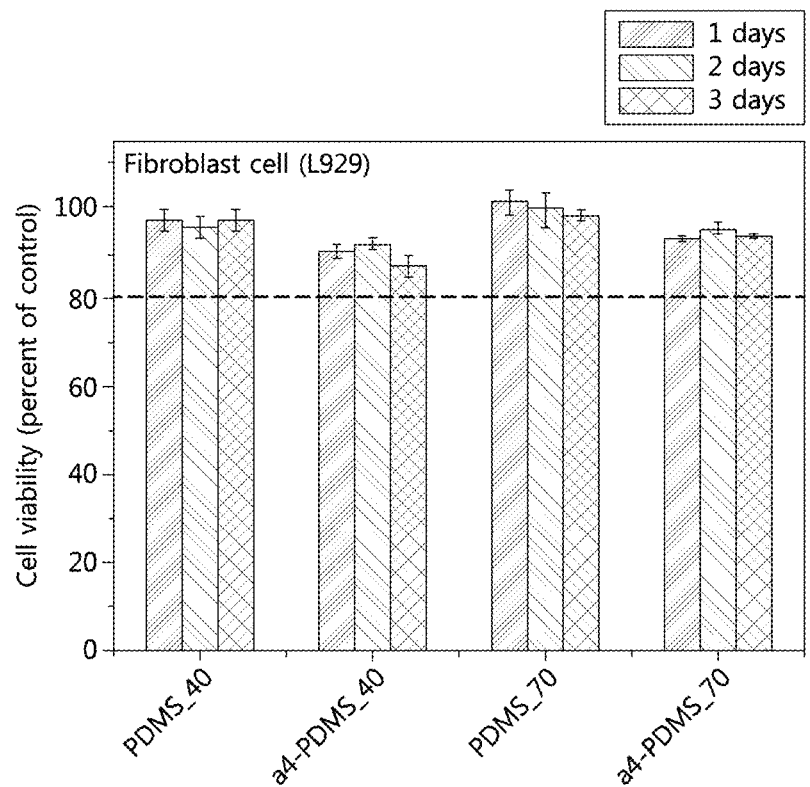
FIGS. 7A and 7B illustrate a result of a cell viability test and optical microscope images of fibroblasts to measure biocompatibility of an adhesive polydimethylsiloxane matrix according to an embodiment of the present disclosure.
Figure 7B:
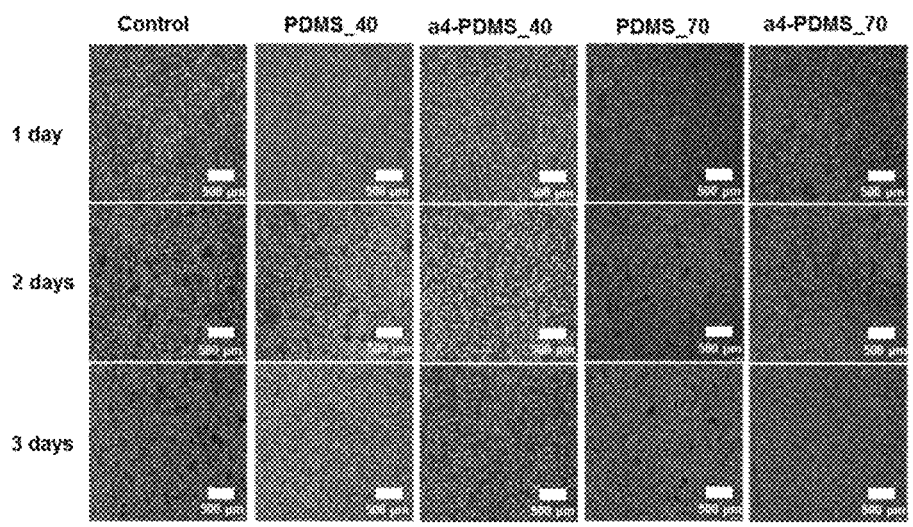
Figure 7C:
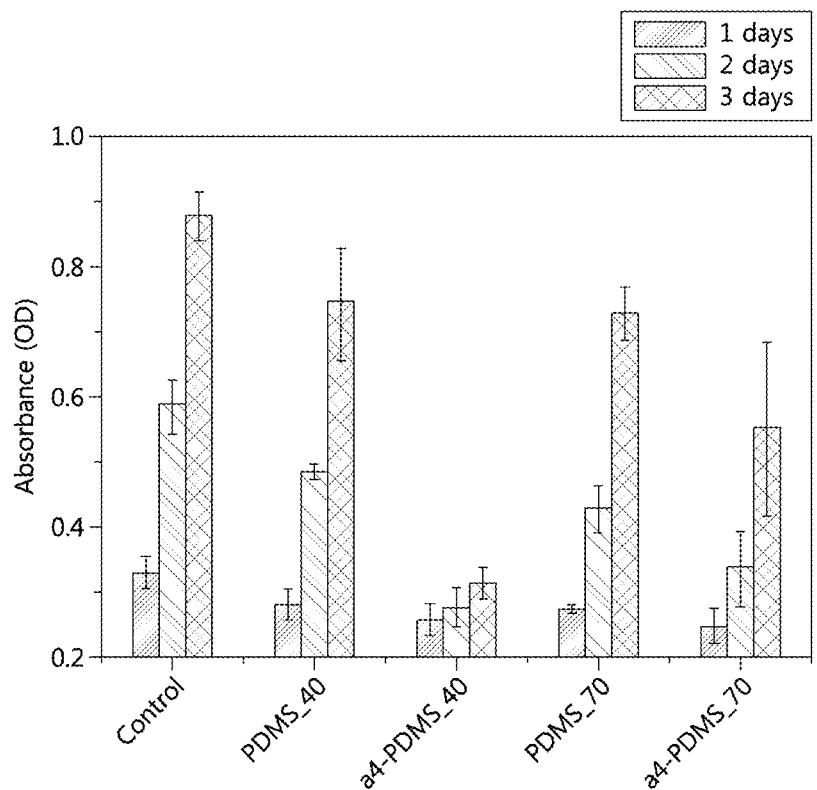
FIG. 7C is a graph illustrating absorbance of fibroblasts.

FIGS. 7A and 7B illustrate a result of a cell viability test and optical microscope images of fibroblasts to measure biocompatibility of an adhesive polydimethylsiloxane matrix according to an embodiment of the present disclosure, and FIG. 7C is a graph illustrating absorbance of fibroblasts.

To measure biocompatibility of the adhesive polydimethylsiloxane matrixes according to an embodiment of the present disclosure (a4-PDMS_40 and a4-PDMS_70 samples were used) and polydimethylsiloxane matrixes (PDMS_40 and PDMS_70 were used), cell viability and proliferation rates were analyzed by indirect methods. Fibroblasts (L929) were grown at 37° C. in a 5% $CO_2$ incubator. The samples were washed with ethanol and by UV exposure. Subsequently, the samples were put in a 24-well plate, and then 1 ml of a solution containing fibroblasts was sprayed thereto.

The density of the fibroblasts in the solution was $10^5$ cells·$ml^{-1}$, cell viability was analyzed using a CCK-8 kit, and absorbance was measured at 450 nm using a microplate reader (VersaMax, Molecular Devices LLC).

Cell viability of a sample is determined by a ratio of the number of cells grown on a surface of the sample to the number of cells grown on a control sample (optimal environment conditions for cell growth). When a cell viability of a sample is 80% or more, the sample is considered biocompatible.

Referring to FIGS. 7A and 7B, all four samples, i.e., PDMS_40 and a4-PDMS_40 heat-hardened at 40° C. and PDMS_70 and a4-PDMS_70 heat-hardened at 70° C., exhibit cell viabilities of 80% or more. From these results, it can be confirmed that Triton X-100 does not affect the biocompatibility of the polydimethylsiloxane matrix.

Referring to FIG. 7C, it can be confirmed that, when Triton X-100 is added and heat hardening temperature is lowered, absorbance is decreased. The absorbance was measured using a CCK-8 kit. Since a CCK-8 kit detects signals of living cells, the absorbance measured by the CCK-8 kit is proportional to a growth rate of cells.

Accordingly, it can be confirmed that addition of Triton X-100 and low heat hardening temperature each independently induce decrease in a cell proliferation rate, and, particularly, the cell proliferation rate on a4-PDMS_40 is considerably low compared to other samples. For cell proliferation, a surface of a sample should be soft enough to allow cells to grow. However, a4-PDMS_40 has high surface roughness, thereby having a low cell proliferation rate.

Figure 8:
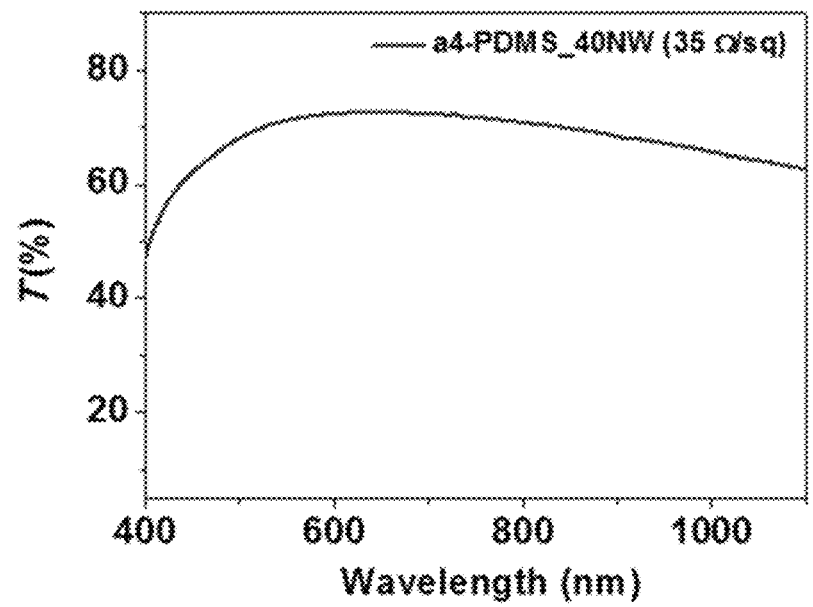
FIG. 8 is a graph illustrating light transmittance of an adhesive transparent electrode based on a silver nanowire-embedded adhesive polydimethylsiloxane matrix according to an embodiment of the present disclosure.

FIG. 8 is a graph illustrating light transmittance of an adhesive transparent electrode based on a silver nanowire-embedded adhesive polydimethylsiloxane matrix according to an embodiment of the present disclosure.

Referring to FIG. 8, it can be confirmed that an adhesive transparent electrode based on a silver nanowire-embedded adhesive polydimethylsiloxane matrix, which has been heat-hardened at 40° C. and includes 0.4% by weight of Triton X-100, exhibits an electrical resistance ($R_S$) of 35 $\Omega \cdot sq^{-1}$ and a light transmittance of about 75%.

Figure 9A:
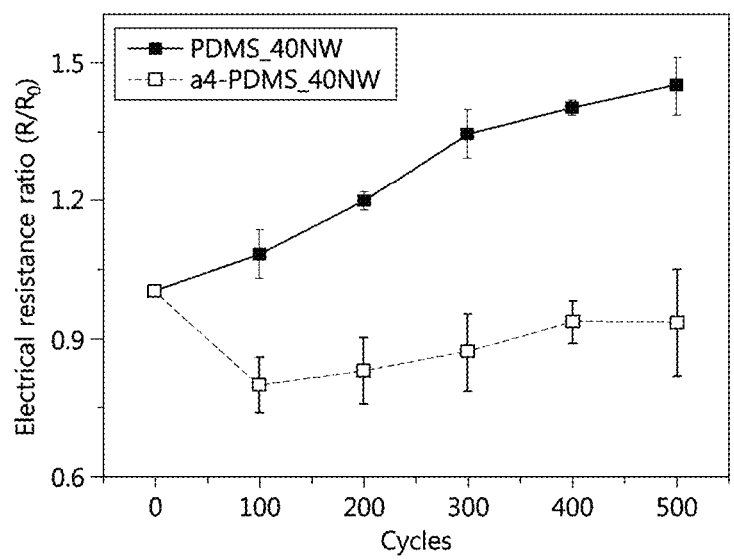
FIG. 9A is a graph illustrating a stretchability test result of an adhesive transparent electrode based on a silver nanowire-embedded adhesive polydimethylsiloxane matrix according to an embodiment of the present disclosure.
Figure 9B:
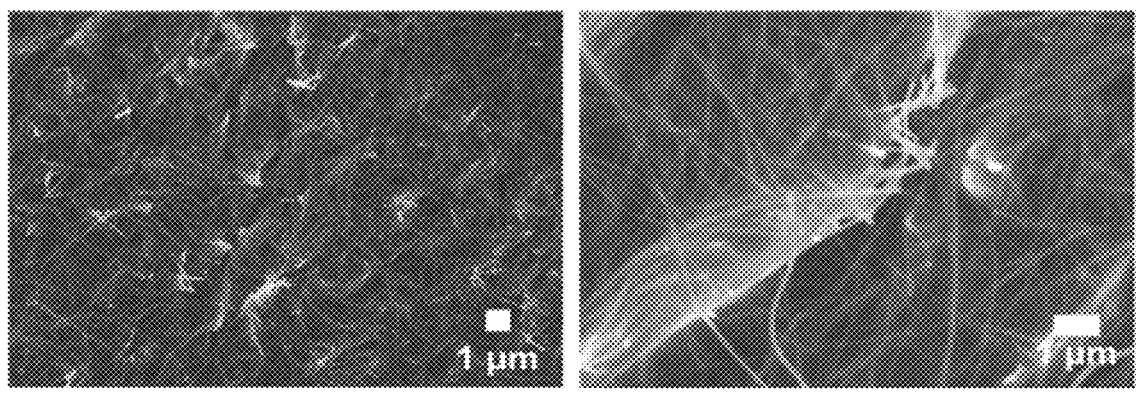
FIGS. 9B and 9C illustrate field emission-scanning electron microscopy (FE-SEM) images before and after stretching of a polydimethylsiloxane matrix-based transparent electrode (PDMS_40NW)
Figure 9C:
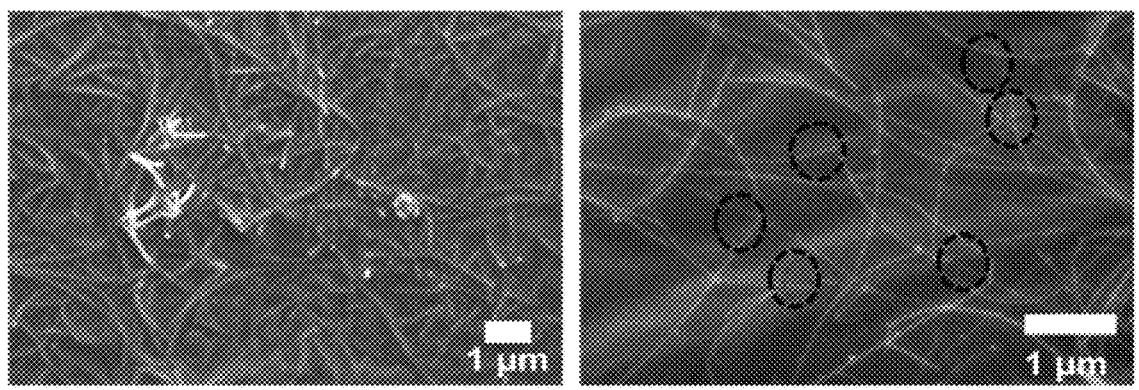
Figure 9D:
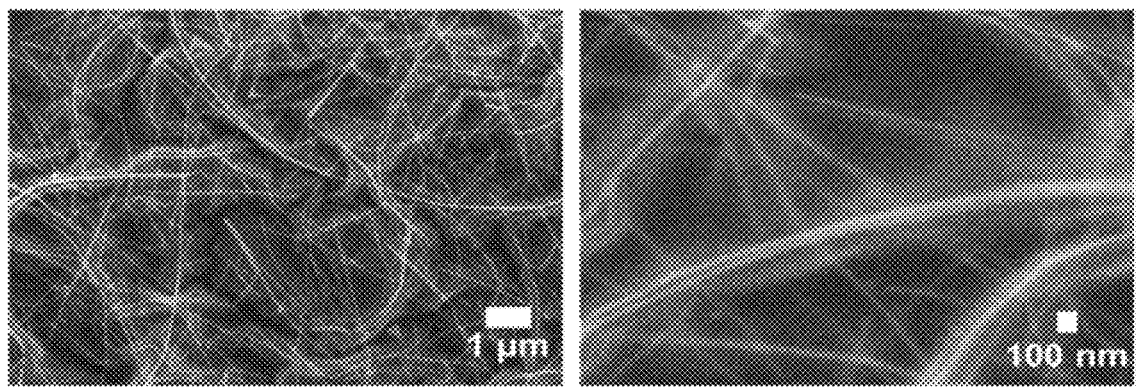
FIGS. 9D and 9E illustrate FE-SEM images before and after stretching of an adhesive polydimethylsiloxane matrix-based transparent electrode (a4-PDMS_40NW)
Figure 9E:
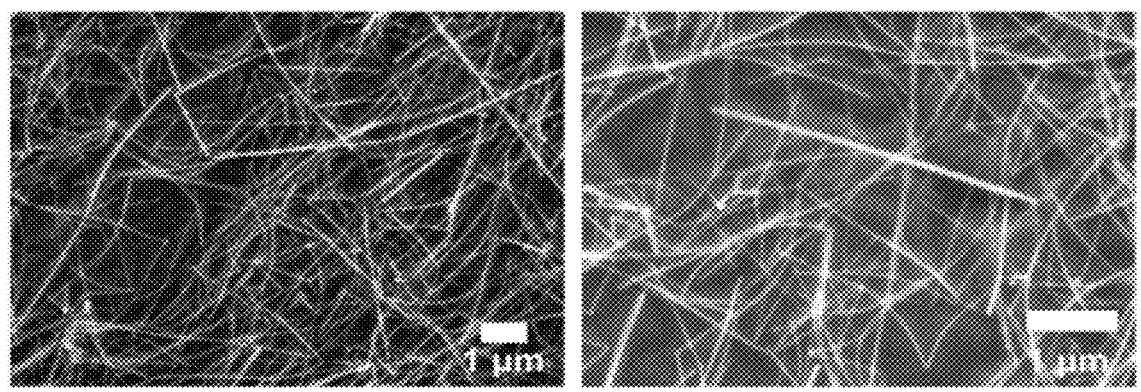

FIG. 9A is a graph illustrating a stretchability test result of an adhesive transparent electrode based on a silver nanowire-embedded adhesive polydimethylsiloxane matrix according to an embodiment of the present disclosure, FIGS. 9B and 9C illustrate field emission-scanning electron microscopy (FE-SEM) images before and after stretching of a polydimethylsiloxane matrix-based transparent electrode (PDMS_40NW), and FIGS. 9D and 9E illustrate FE-SEM images before and after stretching of an adhesive polydimethylsiloxane matrix-based transparent electrode (a4-PDMS_40NW).

For stretchability test, a polydimethylsiloxane matrix-based transparent electrode sample (PDMS_40NW) and a a4-PDMS_40-based transparent electrode sample (a4-PDMS_40NW), which was an adhesive polydimethylsiloxane matrix, were used. This test was performed for 500 cycles at a strain of 12.5%.

The a4-PDMS_40NW sample was only used because an a3-PDMS_40-based transparent electrode sample (a3-PDMS_40NW) exhibited too high electrical resistance to be applied to a transparent electrode.

Referring to FIG. 9A, it can be confirmed that an electrical resistance ratio (R/R$_0$) of a4-PDMS_40NW decreases to 0.8 after 100 cycles and reaches 0.94 after 500 cycles. On the other hand, it can be confirmed that an electrical resistance ratio of PDMS_40NW continues to increase and reaches 1.5 after 500 cycles.

FIGS. 9B to 9E, enlarged portions of left images are illustrated in right images.

Referring to FIG. 9B, it can be confirmed that PDMS_40NW shows severely peeled silver nanowires even before the periodic stretchability test. In addition, referring to a right image of FIG. 9C, silver nanowires are fractured after the periodic stretchability test (indicated by dotted lines). From these images, it can be confirmed that the silver nanowires are not satisfactorily embedded in the polydimethylsiloxane matrix due to low adhesion force between the polydimethylsiloxane matrix and the silver nanowires.

On the other hand, referring to FIG. 9D, it can be confirmed that a4-PDMS_40NW does not show peeling of AgNWs. In addition, referring to FIG. 9E, it can be confirmed that AgNWs are not fractured after the periodic stretchability test. These images indicate that adhesion force between a4-PDMS_40NW and AgNWs is superior to that between PDMS_40NW and AgNWs.

The adhesion force between a4-PDMS_40 and silver nanowires is higher than that between PDMS_40 and silver nanowires because PEG chains of Triton X-100 can participate in electrostatic interactions with silver nanowires.

Stretchability of the a4-PDMS_40NW electrode was improved due to superior adhesiveness between a4-PDMS_40 and silver nanowires. Another reason for the decrease in the electrical resistance ratio after stretching of 100 cycles is that alignment of silver nanowires has been changed in a stretching direction. According to previous research by other researchers, silver nanowires can be aligned in a stretching direction during mechanical stretching.

The silver nanowires inserted in a4-PDMS_40 may be aligned in a stretching direction during periodic stretching because the adhesion force between silver nanowires and a4-PDMS_40 is strong due to Triton X-100.

Hereinafter, the characteristics of a strain sensor and ECG sensor, to which the adhesive transparent electrode based on the silver nanowire-embedded adhesive polydimethylsiloxane matrix according to an embodiment of the present disclosure is applied, are described.

Figure 10A:
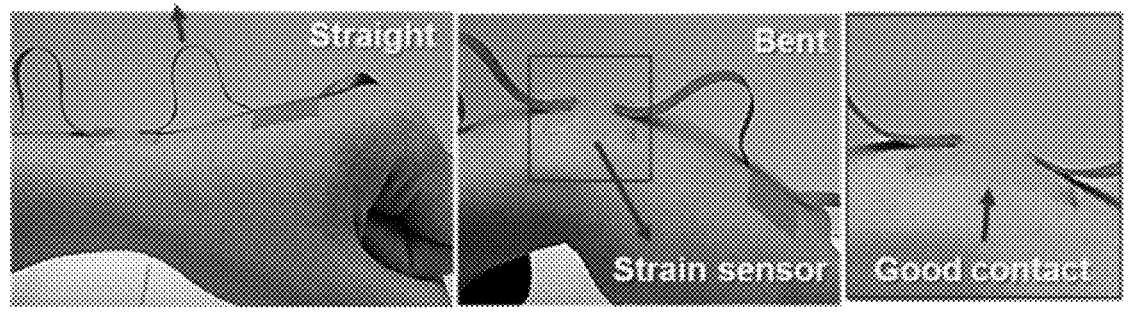
FIG. 10A illustrates photograph of a strain sensor, to which a transparent electrode (a4-PDMS_40NW) based on a silver nanowire-embedded adhesive polydimethylsiloxane matrix according to an embodiment of the present disclosure is applied, attached to the wrist.
Figure 10B:
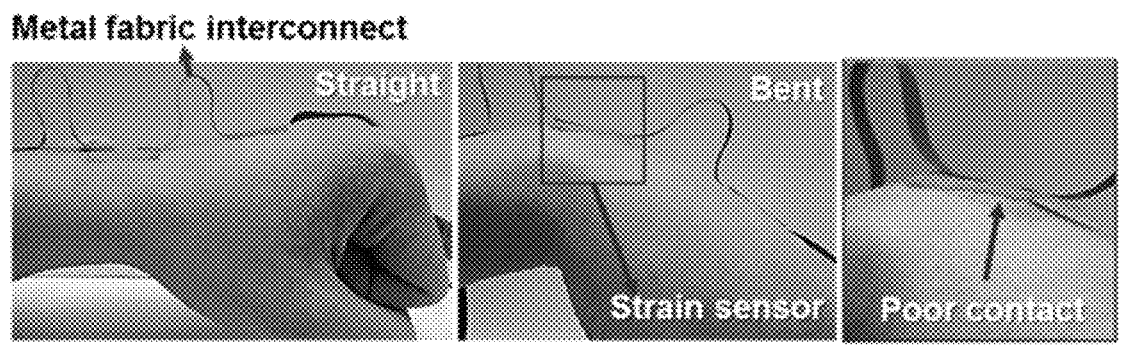
FIG. 10B illustrates photographs of a strain sensor, to which an transparent electrode (PDMS_40NW) based on a silver nanowire-embedded polydimethylsiloxane matrix according to an embodiment of the present disclosure is applied, attached to the wrist.

FIG. 10A illustrates photograph of a strain sensor, to which a transparent electrode (a4-PDMS_40NW) based on a silver nanowire-embedded adhesive polydimethylsiloxane matrix according to an embodiment of the present disclosure is applied, attached to the wrist, and FIG. 10B illustrates photographs of a strain sensor, to which an transparent electrode (PDMS_40NW) based on a silver nanowire-embedded polydimethylsiloxane matrix according to an embodiment of the present disclosure is applied, attached to the wrist.

Referring to FIGS. 10A and 10B, it can be confirmed that a4-PDMS_40NW exhibits perfectly conformal contact with the skin and is not peeled off by repeated bending of the wrist 10 times (a third image of FIG. 10A). However, it can be confirmed that the strain sensor, to which the PDMS_40NW is applied, is peeled off from the skin even by a first bending motion (a second image of FIG. 10B).

Figure 10C:
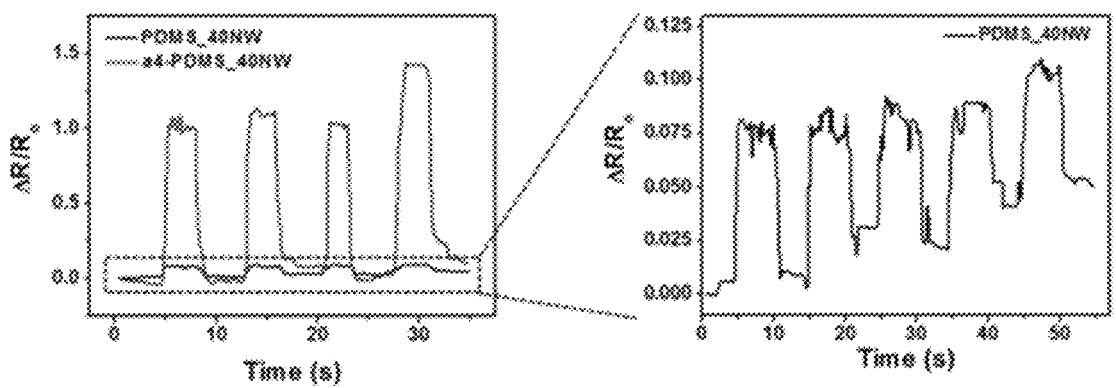
FIG. 10C illustrates a relative resistance change of a strain sensor, to which a transparent electrode (a4-PDMS_40NW) based on a silver nanowire-embedded adhesive polydimethylsiloxane matrix according to an embodiment of the present disclosure is applied, and a relative resistance change of a strain sensor, to which an transparent electrode (PDMS_40NW) based on a silver nanowire-embedded polydimethylsiloxane matrix is applied.

FIG. 10C illustrates a relative resistance change of a strain sensor, to which a transparent electrode (a4-PDMS_40NW) based on a silver nanowire-embedded adhesive polydimethylsiloxane matrix according to an embodiment of the present disclosure is applied, and a relative resistance change of a strain sensor, to which an transparent electrode (PDMS_40NW) based on a silver nanowire-embedded polydimethylsiloxane matrix is applied.

Referring to FIG. 10C, it can be confirmed that a4-PDMS_40NW exhibits a greater electrical resistance change than PDMS_40NW under the same stain applied thereto. This indicates that the sensitivity of a4-PDMS_40NW is significantly higher than that of PDMS_40NW under the fixed strain. Such a difference is caused by higher conformability and stretchability of a4-PDMS_40NW to the skin, compared to PDMS_40NW.

In addition, as shown in FIG. 10C, the strain sensor, to which a4-PDMS_40NW is applied, exhibits low hysteresis, and maintains a relative resistance change ($\Delta R/R_0^{-1}$) of 0 during the periodic bending of the wrist.

However, the strain sensor, to which PDMS_40NW is applied, exhibits high hysteresis that greatly deteriorates performance of the strain sensor, and $\Delta R/R_0^{-1}$ in a straight state continuously increases during multiple bending cycles of the wrist.

Figure 11A:
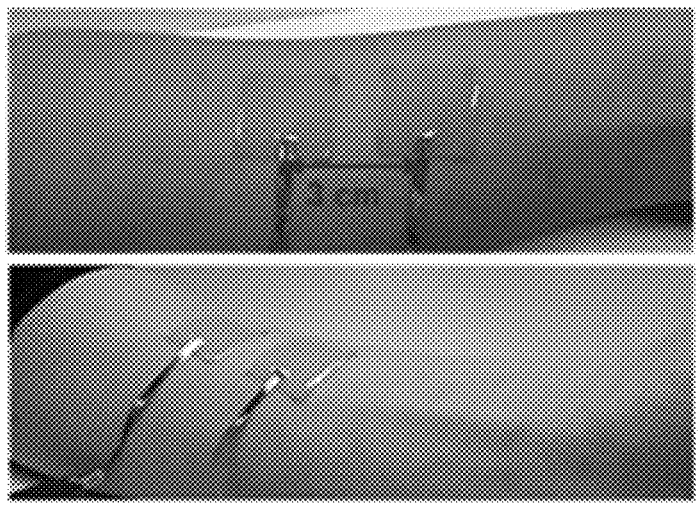
FIGS. 11A to 11C illustrate photographs of ECG sensors, to which a transparent electrode (a4-PDMS_40NW) based on a silver nanowire-embedded adhesive polydimethylsiloxane matrix according to an embodiment of the present disclosure is applied, attached to an arm (FIG. 11A) and photographs of ECG sensors, to which an transparent electrode (PDMS_40NW) based on a silver nanowire-embedded polydimethylsiloxane matrix is applied, attached to an arm, (FIGS. 11B and C)
Figure 11B:
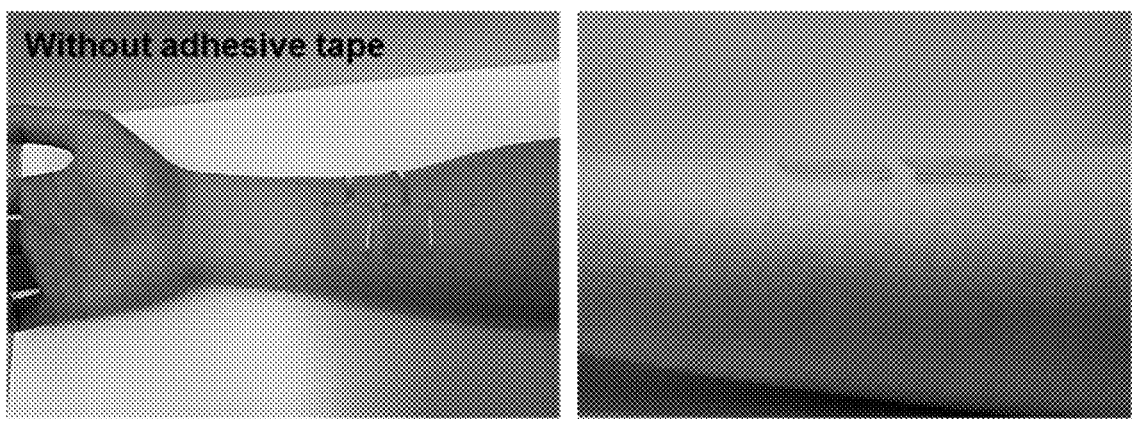
Figure 11C:
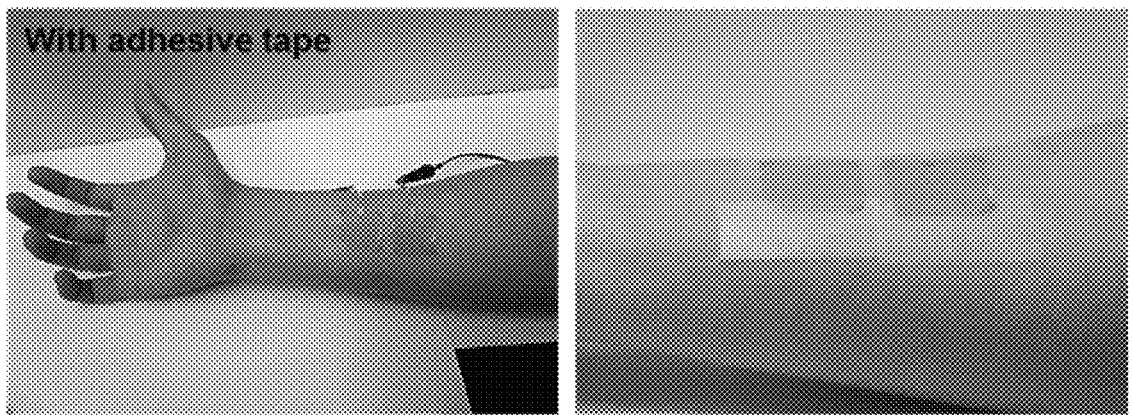
Figure 11D:
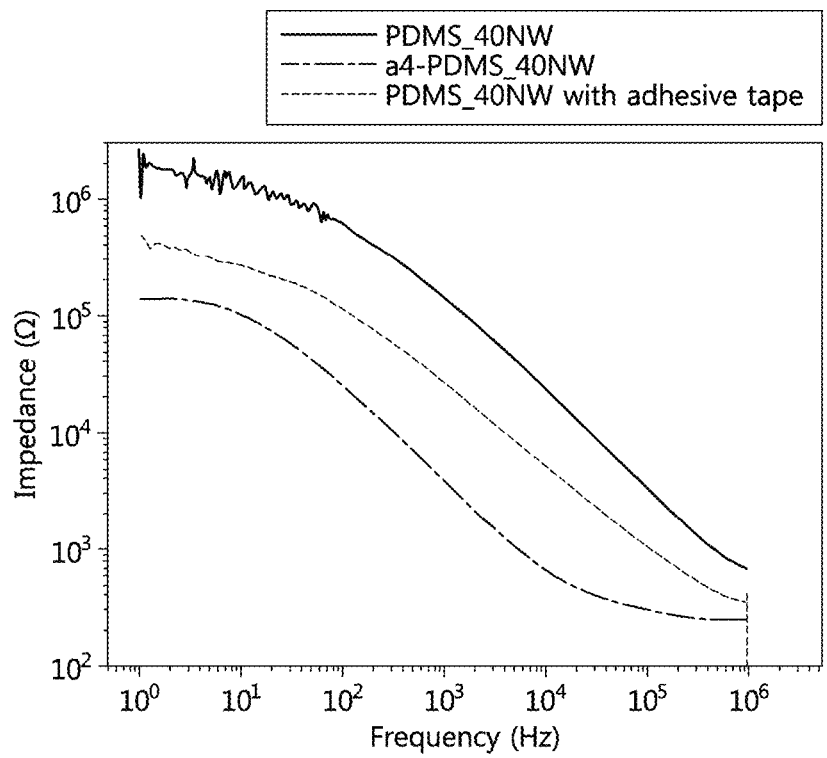
FIG. 11D illustrates skin impedances measured with the ECG sensors.

FIGS. 11A to 11C illustrate photographs of ECG sensors, to which a transparent electrode (a4-PDMS_40NW) based on a silver nanowire-embedded adhesive polydimethylsiloxane matrix according to an embodiment of the present disclosure is applied, attached to an arm (FIG. 11A) and photographs of ECG sensors, to which an transparent electrode (PDMS_40NW) based on a silver nanowire-embedded polydimethylsiloxane matrix is applied, attached to an arm, (FIGS. 11B and C) and FIG. 11D illustrates skin impedances measured with the ECG sensors.

Referring to FIG. 11A, it can be confirmed that ECG sensors, to which a4-PDMS_40NW has been applied, are attached to the arm by a 3 cm interval so as to measure skin impedance, and are well attached to the arm without lifting. In addition, referring to a lower image, the ECG sensors can be confirmed to be well attached to the arm without lifting when observed at a different angle.

On the other hand, referring to FIG. 11B, it can be confirmed that, when the ECG sensors, to which PDMS_40NW has been applied, are attached to the arm without an adhesive tape, the ECG sensors have poor adhesiveness to the skin and thus are easily peeled off. Accordingly, to increase adhesion force thereof to the skin, ECG sensors, to which PDMS_40NW has been applied, were attached using an adhesive tape as shown in FIG. 11C.

Referring to FIG. 11D, it can be confirmed that the ECG sensors, to which PDMS_40NW has been applied, have poor adhesion force to the skin and thus exhibit low conformability, thereby exhibiting a very high skin impedance.

Therefore, it can be confirmed that, when the ECG sensors having poor adhesion force to the skin, to which PDMS_40NW has been applied, are attached to the skin using an adhesive tape, adhesion force thereof to the skin increases, whereby the ECG sensors exhibit a lower skin impedance, compared to the case in which an adhesive tape was not used.

In addition, it can be confirmed that, in the case of the ECG sensors to which a4-PDMS_40NW has been applied, a lower skin impedance is exhibited, compared to the case of the ECG sensors, to which PDMS_40NW has been applied, and the case of the ECG sensors attached using an adhesive tape.

From these results, it can be confirmed that adhesion force to the skin is very important upon recording of ECG signals.

Figure 11E:
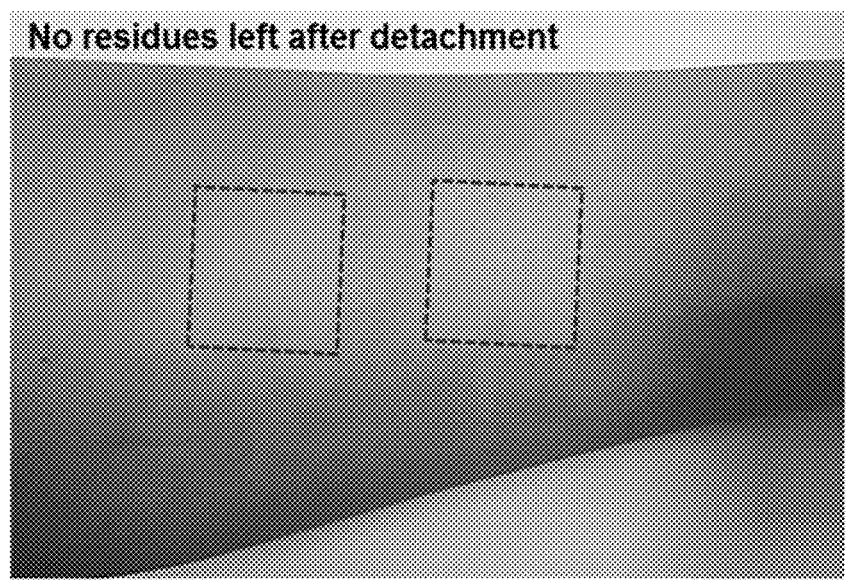
FIG. 11E illustrates a photograph of the skin after detaching the transparent electrode (a4-PDMS_40NW) based on the silver nanowire-embedded adhesive polydimethylsiloxane matrix according to an embodiment of the present disclosure therefrom.

FIG. 11E illustrates a photograph of the skin after detaching the transparent electrode (a4-PDMS_40NW) based on the silver nanowire-embedded adhesive polydimethylsiloxane matrix according to an embodiment of the present disclosure therefrom.

Referring to FIG. 11E, it can be confirmed that there is no residual on the skin after separating a4-PDMS_40NW from the skin, and a residual on the skin does not cause skin irritation or allergic reaction. This indicates that a4-PDMS_40NW may be advantageously applied to an ECG sensor.

Figure 12A:
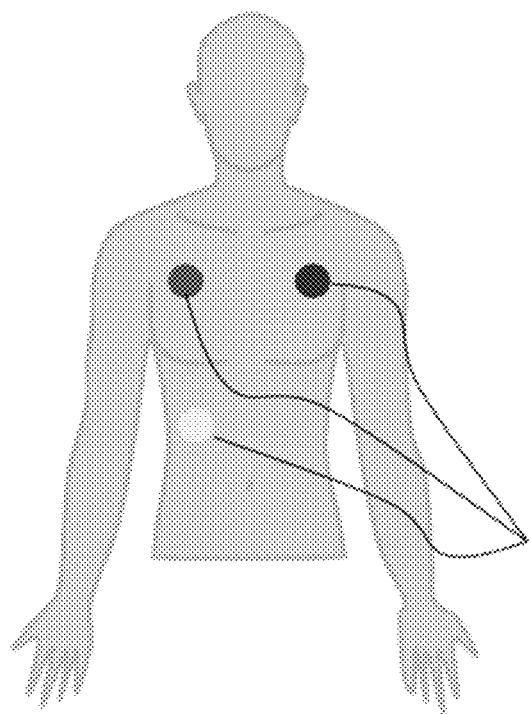
FIG. 12A illustrates electrode positions of an ECG sensor, to which a transparent electrode (a4-PDMS_40NW) based on a silver nanowire-embedded adhesive polydimethylsiloxane matrix according to an embodiment of the present disclosure is applied.

FIG. 12A illustrates electrode positions of an ECG sensor, to which a transparent electrode (a4-PDMS_40NW) based on a silver nanowire-embedded adhesive polydimethylsiloxane matrix according to an embodiment of the present disclosure is applied.

As illustrated in FIG. 12A, three electrodes were respectively attached to a right side of the chest, a left side of the chest, and a lower right side of the thorax so as to measure an electrocardiogram.

Figure 12B:
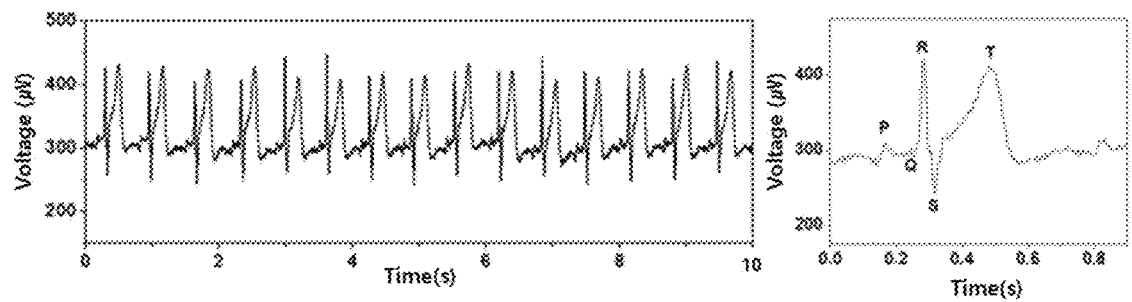
FIG. 12B illustrates electrocardiogram signals measured with an ECG sensor to which a commercial gel is applied.
Figure 12C:
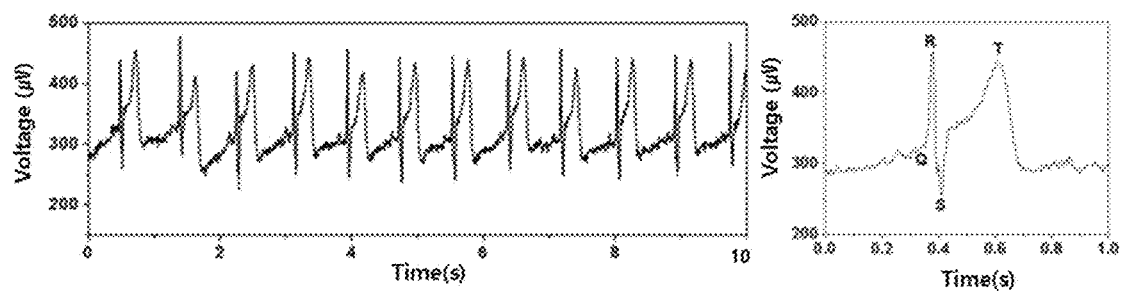
FIG. 12C illustrates electrocardiogram signals measured with an ECG sensor to which an transparent electrode (PDMS_40NW) based on a silver nanowire-embedded polydimethylsiloxane matrix is applied.
Figure 12D:
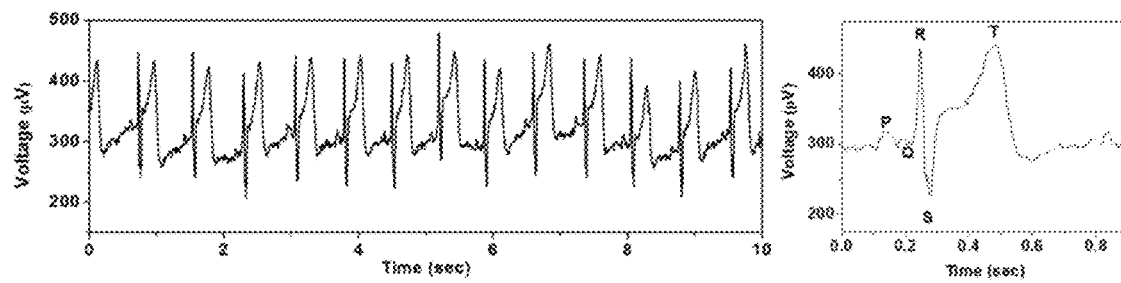
FIG. 12D illustrates electrocardiogram signals measured with an ECG sensor, to which an transparent electrode (PDMS_40NW) based on a silver nanowire-embedded polydimethylsiloxane matrix is applied, attached to the skin using an adhesive tape.
Figure 12E:
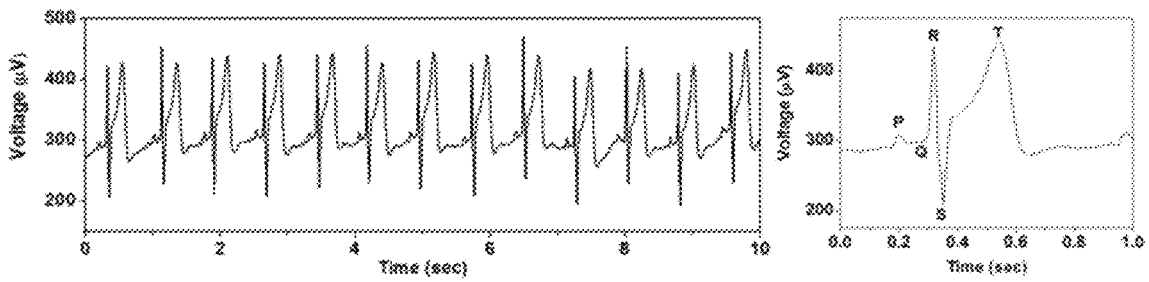
FIG. 12E illustrates electrocardiogram signals measured with an ECG sensor to which a transparent electrode (a4-PDMS_40NW) based on a silver nanowire-embedded adhesive polydimethylsiloxane matrix is applied.

FIG. 12B illustrates electrocardiogram signals measured with an ECG sensor to which a commercial gel is applied, FIG. 12C illustrates electrocardiogram signals measured with an ECG sensor to which an transparent electrode (PDMS_40NW) based on a silver nanowire-embedded polydimethylsiloxane matrix is applied, FIG. 12D illustrates electrocardiogram signals measured with an ECG sensor, to which an transparent electrode (PDMS_40NW) based on a silver nanowire-embedded polydimethylsiloxane matrix is applied, attached to the skin using an adhesive tape, and FIG. 12E illustrates electrocardiogram signals measured with an ECG sensor to which a transparent electrode (a4-PDMS_40NW) based on a silver nanowire-embedded adhesive polydimethylsiloxane matrix is applied.

Referring to FIG. 12B, a P wave of the ECG sensor, to which a commercial gel-based transparent electrode has been applied, is weakly observed. However, referring to FIG. 12C, some signals of the ECG sensor, to which PDMS_40NW has been applied, exhibit low signal noise and such severe noise that a P wave could not be distinguished.

Referring to FIG. 12D, it can be confirmed that, when the ECG sensor, to which PDMS_40NW has been applied, is attached to the skin using an adhesive tape to increase contact of PDMS_40NW to the skin, noise of an ECG signal is slightly reduced, compared to the ECG sensor, to which PDMS_40NW has been applied, illustrated in FIG. 12C, but there is still signal noise.

Referring to FIG. 12E, it can be confirmed that the ECG sensor, to which a4-PDMS_40NW has been applied, exhibits much less ECG signal noise, compared to the ECG sensor to which a commercial gel-based transparent electrode has been applied, illustrated in FIG. 12B.

Figure 13A:
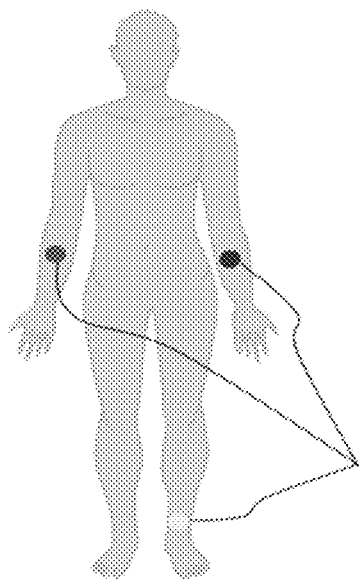
FIG. 13A illustrate positions of ECG sensors to which a transparent electrode (a4-PDMS_40NW) based on a silver nanowire-embedded adhesive polydimethylsiloxane matrix according to an embodiment of the present disclosure is applied.

FIG. 13A illustrate positions of ECG sensors to which a transparent electrode (a4-PDMS_40NW) based on a silver nanowire-embedded adhesive polydimethylsiloxane matrix according to an embodiment of the present disclosure is applied.

As shown in FIG. 13A, three electrodes were respectively attached to both arms and the left ankle to measure an electrocardiogram.

Figure 13B:
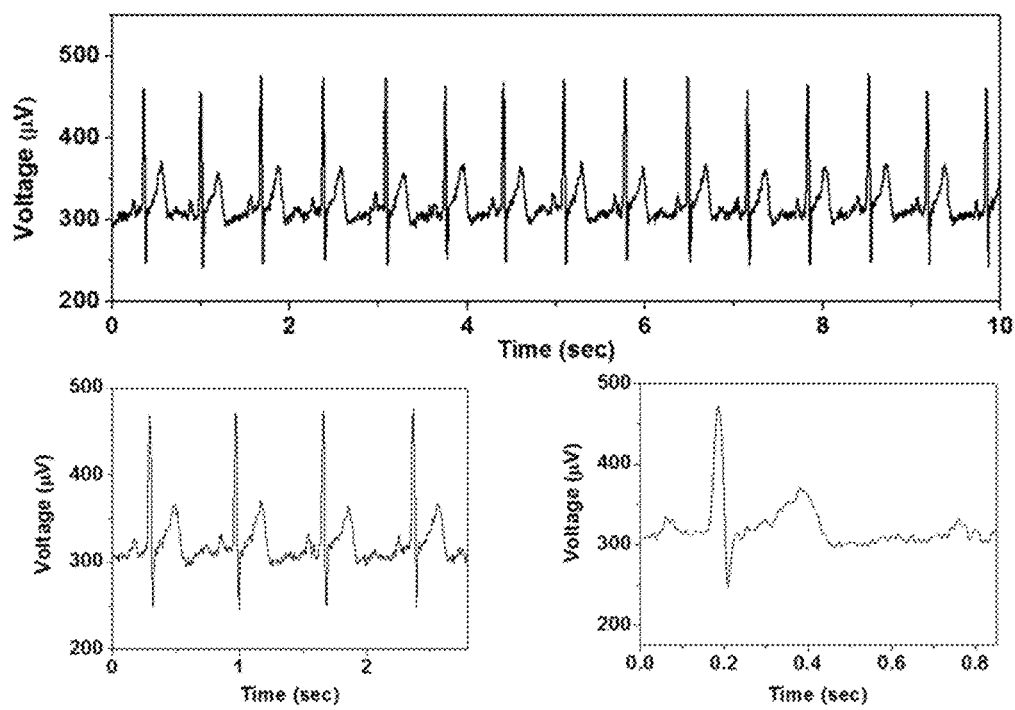
FIG. 13B illustrates electrocardiogram signals measured with an ECG sensor to which a commercial gel is applied.
Figure 13C:
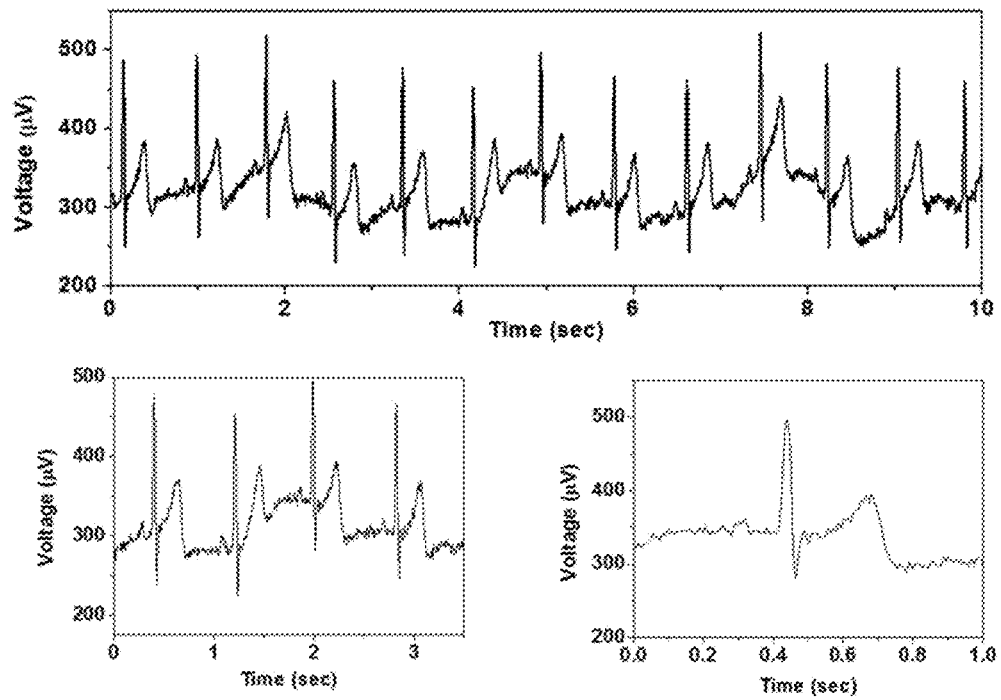
FIG. 13C illustrates electrocardiogram signals measured with an ECG sensor, to which an transparent electrode (PDMS_40NW) based on a silver nanowire-embedded polydimethylsiloxane matrix is applied, attached to the skin using an adhesive tape.
Figure 13D:
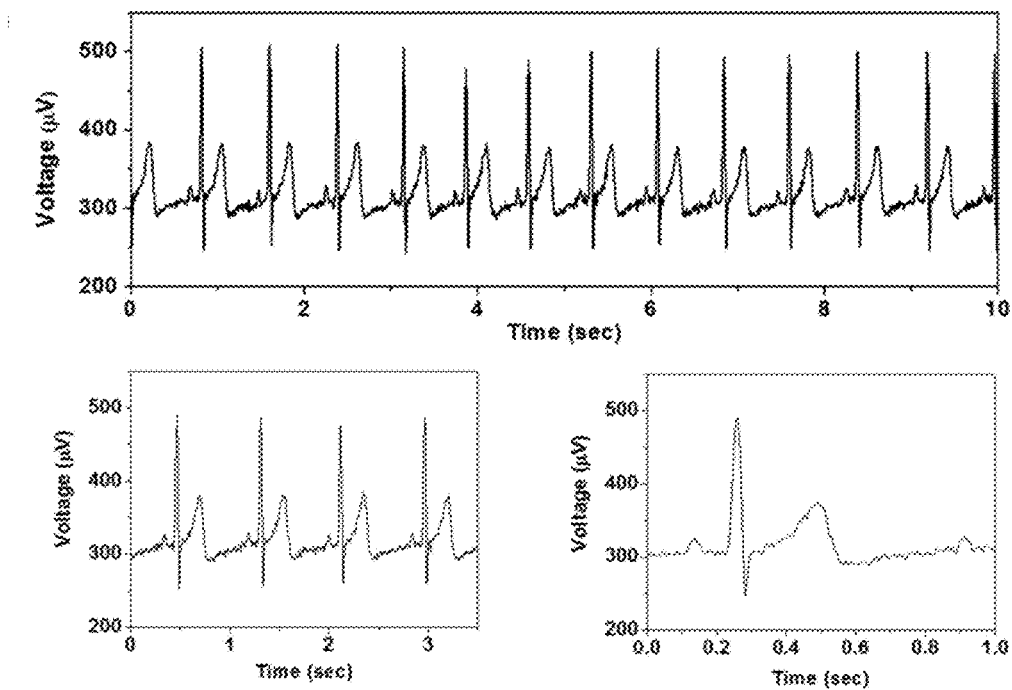
FIG. 13D illustrates electrocardiogram signals measured with an ECG sensor to which a transparent electrode (a4-PDMS_40NW) based on a silver nanowire-embedded adhesive polydimethylsiloxane matrix is applied.

FIG. 13B illustrates electrocardiogram signals measured with an ECG sensor to which a commercial gel is applied, FIG. 13C illustrates electrocardiogram signals measured with an ECG sensor, to which an transparent electrode (PDMS_40NW) based on a silver nanowire-embedded polydimethylsiloxane matrix is applied, attached to the skin using an adhesive tape, and FIG. 13D illustrates electrocardiogram signals measured with an ECG sensor to which a transparent electrode (a4-PDMS_40NW) based on a silver nanowire-embedded adhesive polydimethylsiloxane matrix is applied.

Referring to FIGS. 13B to 13D, it can be confirmed that, when an ECG sensor is attached to the chest, noise of ECG signals is large due to a distance between the electrode and the heart (see FIGS. 12B to 12E).

Referring to FIG. 13C, even though the ECG sensor, to which PDMS_40NW has been applied, is attached using an adhesive tape so as to increase adhesion force to the skin, noise of ECG signals thereof is very severe. This result indicates that the ECG sensor has very poor adhesion to the arm skin.

Referring to FIG. 13D, it can be confirmed that the ECG sensor, to which a4-PDMS_40NW has been applied, exhibits clear and stable ECG signals similar to the ECG sensor to which a commercial gel-based transparent electrode has been applied.

It can be confirmed that the ECG sensor, to which a4-PDMS_40NW has been applied, exhibits low signal noise due to high conformability thereof to the skin and high electrical conductivity of silver nanowires embedded therein.

It can be confirmed that the ECG sensor, to which a4-PDMS_40NW has been applied, exhibits higher adhesion force to the skin, compared to the ECG sensor to which PDMS_40NW has been applied, and considerably increased biocompatibility, compared to the ECG sensor to which a commercial gel-based transparent electrode has been applied.

As described above, a transparent electrode wherein a metal nanowire network is embedded in an adhesive silicone-based polymer matrix including a non-ionic surfactant has very high conformability when applied to an epidermal biosensor.

This indicates that the conformability of the transparent electrode has been increased due to improvement in mechanical properties, such as adhesiveness, compliance, and viscoelasticity, of the adhesive silicone-based polymer matrix included therein.

The mechanical characteristics may be improved by adjusting hardening temperature and adding a non-ionic surfactant, Triton X-100, to cause interaction between a platinum (Pt) catalyst, present in a polydimethylsiloxane crosslinker, and polar functional groups, present in Triton X-100, and thus, hindering crosslinking reaction of polydimethylsiloxane.

In addition, a sensor to which the transparent electrode according to the present disclosure is applied may greatly increase detection sensitivity of various bio-signals such as EMG, EEG, and glucose. Further, the transparent electrode may be used as an electrode material of, other than a biosensor, various wearable electronic devices such as a triboelectric nanogenerator, an optoelectronic device, a transparent film heater, and a wireless antenna.

According to an embodiment of the present disclosure, the properties of a silicone-based polymer can be easily controlled with a very small amount of non-ionic surfactant by using a non-ionic surfactant.

In addition, since a transparent electrode according to an embodiment of the present disclosure has high adhesiveness, the transparent electrode can be attached to the skin without an additional adhesive, and the adhesiveness of the transparent electrode can be maintained even after repeated detachment and attachment.

In addition, according to an embodiment of the present disclosure, the transparent electrode can be fabricated only through heat-hardening of a silicone-based polymer, unlike a conventional method of forming an electrode on a hardened polymer substrate in another coating process, etc.

In addition, according to an embodiment of the present disclosure, electrical conductivity can be maintained even under high strain due to the electrical characteristics of a metal nanowire network.

Although the present disclosure has been described through limited examples and figures, the present disclosure is not intended to be limited to the examples. Those skilled in the art will appreciate that various modifications, additions and substitutions are possible, without departing from the scope and spirit of the disclosure. Therefore, it should be understood that there is no intent to limit the disclosure to the embodiments disclosed, rather, the disclosure is to cover all modifications, equivalents, and alternatives falling within the spirit and scope of the disclosure as defined by the claims.

What is claimed is:

1. An adhesiveness transparent electrode comprising an adhesive silicone-based polymer matrix in which a metal nanowire network is embedded,
    wherein the adhesive silicone-based polymer matrix comprises a silicone-based polymer comprising a silicone-based polymer base and a silicone-based polymer crosslinker; and a non-ionic surfactant,
    wherein a weight ratio of the silicone-based polymer base to the silicone-based polymer crosslinker is 10:1, and a weight ratio of the non-ionic surfactant in the adhesive silicone-based polymer matrix is from 0.3 wt % to 0.4 wt %,
    wherein the adhesive silicone-based polymer matrix comprises a heterogeneously crosslinked network composed of crosslinked silicone-based polymer and non-crosslinked silicone-based polymer and formed in the adhesive silicone-based polymer matrix by the non-ionic surfactant,
    wherein Young's modulus and adhesion force of the adhesive silicone-based polymer matrix having the heterogeneously crosslinked network formed therein is modulated by adding the non-ionic surfactant, and
    wherein Young's modulus of the adhesive silicone-based polymer matrix is in a range of 31.7 kPa to 45 kPa.

2. The adhesiveness transparent electrode according to claim 1, wherein the adhesive transparent electrode is fabricated by coating a dispersing solution comprising the silicone-based polymer base, the silicone-based polymer crosslinker, and the non-ionic surfactant on a substrate on which the metal nanowire network is formed,
    heat-hardening the coated dispersing solution to form the adhesive silicone-based polymer matrix in which the metal nanowire network is embedded, and
    separating the adhesive silicone-based polymer matrix from the substrate.

3. The adhesiveness transparent electrode according to claim 1, wherein crosslinking reaction of the silicone-based polymer is hindered and mechanical characteristics of the adhesive silicone-based polymer matrix are improved, due to interaction between a platinum (Pt) catalyst, present in the silicone-based polymer crosslinker, and polar functional groups, present in the non-ionic surfactant.

4. The adhesiveness transparent electrode according to claim 1, wherein the metal nanowire network is embedded in the adhesive silicone-based polymer matrix due to interaction between polar functional groups, present in the non-ionic surfactant, and polar functional groups, present in the metal nanowire network.

5. The adhesiveness transparent electrode according to claim 1, wherein the non-ionic surfactant is 4-(1,1,3,3-tetramethylbutyl)phenyl-polyethylene glycol.

6. The adhesiveness transparent electrode according to claim 1, wherein the silicone-based polymer is polydimethylsiloxane (PDMS).

7. A method of fabricating an adhesive transparent electrode, the method comprising:
    forming a metal nanowire network on a substrate;
    coating a dispersing solution comprising a silicone-based polymer base, a silicone-based polymer crosslinker, and a non-ionic surfactant on the substrate on which the metal nanowire network is formed; and
    heat-hardening the dispersing solution coated on the substrate, on which the metal nanowire network is formed, to form an adhesive silicone-based polymer matrix in which the metal nanowire network is embedded,
    wherein a weight ratio of the silicone-based polymer base to the silicone-based polymer crosslinker is 10:1, and a weight ratio of the non-ionic surfactant in the adhesive silicone-based polymer matrix is from 0.3 wt % to 0.4 wt %,
    wherein the adhesive silicone-based polymer matrix comprises a heterogeneously crosslinked network composed of crosslinked silicone-based polymer and non-crosslinked silicone-based polymer and formed in the adhesive silicone-based polymer matrix by the non-ionic surfactant,
    wherein Young's modulus and adhesion force of the adhesive silicone-based polymer matrix having the heterogeneously crosslinked network formed therein is modulated by adding the non-ionic surfactant, and
    wherein Young's modulus of the adhesive silicone-based polymer matrix is in a range of 31.7 kPa to 45 kPa.

8. The method according to claim 7, further comprising separating the adhesive silicone-based polymer matrix, in which the metal nanowire network is embedded, from the substrate.

9. The method according to claim 7, wherein the forming comprises:
    coating a metal nanowire solution on the substrate; and
    annealing the substrate coated with the metal nanowire solution.

10. The method according to claim 7, wherein the silicone-based polymer is polydimethylsiloxane, and the metal nanowire network is a silver (Ag) nanowire network.

11. The method according to claim 9, wherein the annealing is performed at 100° C. to 180° C. for 5 minutes to 20 minutes.

12. The method according to claim 10, wherein the heat hardening is performed at 40° C. to 80° C. for 8 hours to 12 hours.

13. An optoelectronic device, an electrocardiogram (ECG) sensor, an electromyogram (EMG) sensor and a transparent film heater to which the adhesive transparent electrode according to claim 1 is applied.

* * * * *

UNITED STATES PATENT AND TRADEMARK OFFICE
CERTIFICATE OF CORRECTION

PATENT NO. : 11,653,510 B2
APPLICATION NO. : 16/169174
DATED : May 16, 2023
INVENTOR(S) : Jin Woo Park and Jin Hoon Kim It is certified that error appears in the above-identified patent and that said Letters Patent is hereby corrected as shown below:

On the Title Page

Item (73) Assignee: "INDUSTRY-ACADEMIC COOPERATION FOUNDATION, YONSEI UNIVERSITY (Seoul, Korea)" has been replaced with --ASEN COMPANY, (Seoul, Korea)--

Signed and Sealed this
Twelfth Day of November, 2024

Katherine Kelly Vidal
*Director of the United States Patent and Trademark Office*